(12) United States Patent
Yu et al.

(10) Patent No.: US 9,175,322 B2
(45) Date of Patent: Nov. 3, 2015

(54) STABLE BACTERIAL CULTURES FOR PRODUCING ALGINATES

(75) Inventors: Hongwei D. Yu, Huntington, WV (US); Dongru Qiu, Norman, OK (US); F. Heath Damron, Huntington, WV (US)

(73) Assignee: Marshall University Research Corporation, Huntington, WV (US)

( * ) Notice: Subject to any disclaimer, the term of this patent is extended or adjusted under 35 U.S.C. 154(b) by 1065 days.

(21) Appl. No.: 12/432,474

(22) Filed: Apr. 29, 2009

(65) Prior Publication Data

US 2011/0184157 A1   Jul. 28, 2011

Related U.S. Application Data

(60) Provisional application No. 61/048,858, filed on Apr. 29, 2008.

(51) Int. Cl.
*C12P 19/04* (2006.01)
*C12N 1/20* (2006.01)

(52) U.S. Cl.
CPC .. *C12P 19/04* (2013.01); *C12N 1/20* (2013.01)

(58) Field of Classification Search
CPC .......... C12P 19/04; C12N 1/20; C12N 15/63; C12N 15/78
USPC .......................... 435/101, 252.34, 320.1, 471
See application file for complete search history.

(56) References Cited

U.S. PATENT DOCUMENTS

| | | |
|---|---|---|
| 4,110,162 A | 8/1978 | Righelato et al. |
| 4,130,461 A | 12/1978 | Righelato et al. |
| 4,235,966 A | 11/1980 | Jarman et al. |
| 4,326,052 A | 4/1982 | Kang et al. |
| 4,326,053 A | 4/1982 | Kang et al. |
| 4,377,636 A | 3/1983 | Kang et al. |
| 4,385,123 A | 5/1983 | Kang et al. |
| 4,490,467 A | 12/1984 | Jarman et al. |
| 4,638,059 A | 1/1987 | Sutherland |
| 4,683,195 A | 7/1987 | Mullis et al. |
| 4,990,601 A | 2/1991 | Skjak-Braek et al. |
| 5,139,945 A | 8/1992 | Liu |
| 5,308,761 A | 5/1994 | Day et al. |
| 5,444,160 A | 8/1995 | Day et al. |
| 5,539,133 A | 7/1996 | Kohn et al. |
| 5,573,910 A | 11/1996 | Deretic et al. |
| 5,591,838 A | 1/1997 | Deretic et al. |
| 5,648,313 A | 7/1997 | Pohl |
| 5,716,829 A | 2/1998 | Rosok et al. |
| 5,912,151 A | 6/1999 | Pollock et al. |
| 5,939,289 A | 8/1999 | Ertesvag et al. |
| 5,994,072 A | 11/1999 | Lam et al. |
| 6,083,691 A | 7/2000 | Deretic et al. |
| 6,121,441 A | 9/2000 | Simensen et al. |
| 6,426,187 B1 | 7/2002 | Deretic et al. |
| 6,455,031 B1 | 9/2002 | Davies et al. |
| 6,551,795 B1 | 4/2003 | Rubenfield et al. |
| 6,852,255 B2 | 2/2005 | Yang et al. |
| 6,881,838 B2 | 4/2005 | Gaddy et al. |
| 6,962,813 B2 | 11/2005 | Pier et al. |
| 7,045,354 B2 | 5/2006 | McDonald et al. |
| 2002/0064858 A1 | 5/2002 | Yacoby-Zeevi |
| 2003/0124631 A1 | 7/2003 | Pier et al. |
| 2004/0091494 A1 | 5/2004 | Pier et al. |
| 2004/0266749 A1 | 12/2004 | Hassett et al. |
| 2005/0038237 A1 | 2/2005 | Hjelland |
| 2008/0085282 A1 | 4/2008 | Yu et al. |

FOREIGN PATENT DOCUMENTS

| | | |
|---|---|---|
| WO | WO 98/40511 A1 | 9/1998 |
| WO | WO 9955368 A1 * | 11/1999 |
| WO | WO 2007/123721 A2 | 11/2007 |

OTHER PUBLICATIONS

Abdel-Fattah et al., Process Biochem. 38:115-122, 2002.*
Govan et al., J. Clin. Microbiol. 30:595-599, 1992.*
O'Toole et al., Mol. Microbiol. 28:449-461, 1998.*
Head, N. "Regulation of Biofilm Formation of *Pseudomonas aeruginosa*", Dissertation, Marshall University, May 2006.*
Qiu et al., Microbiol. 154:2119-2130, 2008.*
Patrauchan et al., Microbiol. 153:3838-3851, 2007.*
O'Toole et al., Molecular Microbiol. 28:449-461, 1998.*
Remminghorst et al., Biotechnol. Lett. 28:1701-1712, 2006.*
Moyano et al., PLoS One 7:e8203, 10 pages, 2009.*
Joshi et al., Nat. Struct. Mol. Biol. 11:404-411, 2004.*
Wozniak et al., PNAS 100:7907-7912, 2003.*
Shanks et al., Appl. Environ. Microbiol. 72:5027-5036, 2006.*
Govan, J.R.W. et al., "Microbial Pathogenesis in Cystic Fibrosis: Mucoid *Pseudomonas aeruginosa* and *Burkholderia cepacia*", *Microbiological Reviews*, Sep. 1996, p. 539-574, vol. 60, No. 30, American Society for Microbiology, Washington, DC.
Ramsey, Deborah M. et al., "Understanding the control of *Pseudomonas aeruginosa* alginate synthesis and the prospects for management of chronic infections in cystic fibrosis", *Molecular Microbiology*, 2005, pp. 309-322, vol. 56, No. 2, Blackwell Publishing Ltd, Oxford, UK.
Martin, D.W. et al., "Mechanism of conversion to mucoidy in *Psedomonas aeruginosa* infecting cystic fibrosis patients", *Proceedings of the National Academy of Sciences of the United States of America*, 1993 Sep. 15, pp. 8377-8381, vol. 90, No. 18, Department of Microbiology, San Antonio, TX.
DeVries, Caroline A. et al., "Mucoid-to-Nonmucoid Conversion in Alginate-Producing *Pseudomonas aeruginosa* Often Results from Spontaneous Mutations in algT, Encoding a Putative Alternate Sigma Factor, and Shows Evidence for Autoregulation", *Journal of Bacteriology*, Nov. 1994, pp. 6677-6687, vol. 176, No. 21, American Society for Microbiology, Washington, DC.
Ma, Sheng et al., "Identification of the Histidine Protein Kinase KinB in *Pseudomonas aeruginosa* and Its Phosphorylation of the Alginate Regulator AlgB", *The Journal of Biological Chemistry*, Jul. 18, 1997, pp. 17952-17960, vol. 272, No. 29, U.S.A.

(Continued)

*Primary Examiner* — David J Steadman
(74) *Attorney, Agent, or Firm* — Stites & Harbison PLLC; Terry L. Wright

(57) ABSTRACT

Methods for mass producing bacterial alginate, bacterial cultures for producing alginate, and pharmaceutical compositions containing bacterial alginate are contemplated.

9 Claims, 10 Drawing Sheets

(56) References Cited

OTHER PUBLICATIONS

Yu, H. et al., "Identification of the algZ Gene Upstream of the Response Regulator algR and Its Participation in Control of Alginate Production in *Pseudomonas aeruginosa*", *Journal of Bacteriology*, Jan. 1997, pp. 187-193, vol. 179, No. 1, American Society for Microbiology, Washington, D.C.

Ma, Sheng et al., "Phosphorylation-Independent Activity of the Response Regulators AlgB and AlgR in Promoting Alginate Biosynthesis in Mucoid *Pseudomonas aeruginosa*", *Journal of Bacteriology*, Feb. 1998, pp. 956-968, vol. 180, No. 4, American Society for Microbiology, Washington, D.C.

Schurr, M.J. et al., "Control of AlgU, a Member of the $\alpha^E$-Like Family of Stress Sigma Factors, by the Negative Regulators MucA and MucB and *Pseudomonas aeruginosa* Conversion to Mucoidy in Cystic Fibrosis", *Journal of Bacteriology*, Aug. 1996, pp. 4997-5004, vol. 178, No. 16, American Society for Microbiology, Washington, D.C.

Mathee, Kalai et al., "Mucoid conversion of *Pseudomonas aeruginosa* by hydrogen peroxide: a mechanism for virulence activation in the cystic fibrosis lung", *Microbiology*, Jun. 1999, pp. 1349-1357, vol. 145, Part 6, SGM, Great Britain.

Anthony, Mario et al., "Genetic Analysis of *Pseudomonas aeruginosa* Isolates from the Sputa of Australian Adult Cystic Fibrosis Patients", *Journal of Clinical Microbiology*, Aug. 2002, pp. 2772-2778, vol. 40, No. 8, American Society for Microbiology, Washington, D.C.

Boucher, J.C. et al., "Mucoid *Pseudomonas aeruginosa* in Cystic Fibrosis: Characterization of muc Mutations in Clinical Isolates and Analysis of Clearance in a Mouse Model of Respiratory Infection", *Infection and Immunity*, Sep. 1997, pp. 3838-3846, vol. 65, No. 9, American Society for Microbiology, Washington, D.C.

Mathee, Kalai et al., "Posttranslational Control of the algT (algU)-Encoded $\alpha^{22}$ for Expression of the Alginate Regulon in *Pseudomonas aeruginosa* and Localization of Its Antagonist Proteins MucA and MucB (AlgN)", *Journal of Bacteriology*, Jun. 1997, pp. 3711-3720, vol. 179, No. 11, American Society for Microbiology, Washington, DC.

Rowen, D.W. et al., "Membrane-to-cytosol redistribution of ECF sigma factor AlgU and conversion to mucoidy in *Pseudomonas aeruginosa* isolates from cystic fibrosis patients", *Molecular Microbiology*, Apr. 2000, pp. 314-327, vol. 36, No. 2, Blackwell Science Ltd., Oxford, UK.

Boucher, J.C. et al., "*Pseudomonas aeruginosa* in cystic fibrosis: role of mucC in the regulation of alginate production and stress sensitivity", *Microbiology*, Nov. 1997, pp. 3473-3480, vol. 143, SGM, Great Britain.

Boucher, J.C. et al., "Two Distinct Loci Affecting Conversion to Mucoidy in *Pseudomonas aeruginosa* in Cystic Fibrosis Encode Homologs of the Serine Protease HtrA", *Journal of Bacteriology*, Jan. 1996, pp. 511-523, vol. 178, No. 2, American Society for Microbiology, Washington, D.C.

Yorgey, Peter et al., "The roles of mucD and alginate in the virulence of *Pseudomonas aeruginosa* in plants, nematodes and mice", Molecular Microbiology, Sep. 2001, pp. 1063-1076, vol. 41, No. 5, Blackwell Science Ltd, Oxford, UK.

Flynn, JoAnne L. et al., "Cloning of Genes from Mucoid *Pseudomonas aeruginosa* Which Control Spontaneous Conversion to the Alginate Production Phenotype", *Journal of Bacteriology*, Apr. 1988, pp. 1452-1460, vol. 170, No. 4, American Society for Microbiology, Washington, D.C.

Govan, J.R. et al., "Isolation of Alginate-producing Mutants of *Pseudomonas fluorescens, Pseudomonas putida* and *Pseudomonas mendocina*", *Journal of General Microbiology*, Jan. 8, 1981, pp. 217-220, vol. 125, SGM, Great Britain.

Conti, Elena et al., "Alginate from *Pseudomonas fluorescens* and *P. putida*: production and properties", *Microbiology*, 1994, pp. 1125-1132, vol. 140, No. 5, SGM, Great Britain.

Knutson, Clarence A. et al., "A New Modification of the Carbazole Analysis: Application to Heteropolysaccharides", *Analytical Biochemistry*, 1968, pp. 470-481, vol. 24, Elsevier Inc, Amsterdam, Netherlands.

Sanchez-Machado, D.I. et al., "Determination of the uronic acid composition of seaweed dietary fibre by HPLC", *Biomedical Chromatography*, Nov. 25, 2003, pp. 90-97, vol. 18, Issue 2, John Wiley & Sons, Ltd., Hoboken, New Jersey.

Wu, Weihui et al., "MucA-Mediated Coordination of Type III Secretion and Alginate Synthesis in *Pseudomonas aeruginosa*", Journal of Bacteriology, Nov. 2004, pp. 7575-7585, vol. 186, No. 22, American Society for Microbiology, Washington, D.C.

Bragonzi, Alessandra et al., "Nonmucoid *Pseudomonas aeruginosa* Expresses Alginate in the Lungs of Patients with Cystic Fibrosis and in a Mouse Model", *The Journal of Infectious Disease*, Aug. 1, 2005, pp. 410-419, vol. 192, No. 3, University of Chicago Press, Chicago, IL.

Head, Nathan E. et al., "Cross-Sectional Analysis of Clinical and Environmental Isolates of *Pseudomonas aeruginosa*: Biofilm Formation, Virulence, and Genome Diversity", *Infection and Immunity*, Jan. 2004, pp. 133-144, vol. 72, No. 1, American Society for Microbiology, Washington, D.C.

"*Pseudomonas aeruginosa* strain PAO581 AlgU (algU), MucA25 mutant (mucA25), MucB (mucB), MucC (mucC), and MucD (mucD) genes, complete cds", GenBank Accession No. EF635219, Jul. 7, 2008.

"Tc1/himar1 mariner transposon vector pFAC plasmid pFAC, complete sequence", GenBank Accession No. DQ366300, May 9, 2007.

Fyfe, Janet A. et al., "Alginate Synthesis in Mucoid *Pseudomonas aeruginosa*: a Chromosomal Locus Involved in Control", *Journal of General Microbiology*, Aug. 1980, pp. 443-450, vol. 119, SGM, Great Britain.

Coleman, Fadie T. et al., "Hypersusceptibility of cystic fibrosis mice to chronic *Pseudomonas aeruginosa* oropharyngeal colonization and lung infection", *Proceedings of the National Academy of Sciences*, Feb. 18, 2003, pp. 1949-1954, vol. 100, No. 4, The National Academy of Sciences, Washington, D.C.

Qiu, Dongru et al., "Regulated proteolysis controls mucoid conversion in *Pseudomonas aeruginosa*", *Proceedings of the National Academy of Sciences*, May 8, 2007, pp. 8107-8112, vol. 104, No. 19, The National Academy of Sciences, Washington, D.C.

Rubin, Eric J. et al., "In vivo transposition of mariner-based elements in enteric bacteria and mycobacteria", *Proceedings of the National Academy of Sciences*, Feb. 1999, pp. 1645-1650, vol. 96, The National Academy of Sciences, Washington, D.C.

Wong, Sandy M. et al., "Genetic footprinting with mariner-based transposition in *Pseudomonas aeruginosa*", *Proceedings of the National Academy of Sciences*, Aug. 29, 2000, pp. 10191-10196, vol. 97, No. 18, The National Academy of Sciences, Washington, D.C.

Deretic, V. et al., "The algR Gene, Which Regulates Mucoidy in *Pseudomonas aeruginosa*, Belongs to a Class of Environmentally Responsive Genes", *Journal of Bacteriology*, Mar. 1989, pp. 1278-1283, vol. 171, No. 3, American Society for Microbiology, Washington, D.C.

Goldberg, J.B. et al., "*Pseudomonas aeruginosa* AlgB, which modulates the expression of alginate, is a member of the NtrC subclass of prokaryotic regulators", *Molecular Microbiology*, Jan. 1992, pp. 59-66, vol. 6, No. 1, Blackwell Science Ltd., Oxford, UK.

Baynham, Patricia J. et al., "Identification and characterization of AlgZ, an AlgT-dependent DNA-binding protein required for *Pseudomonas aeruginosa* algD transcription", *Molecular Microbiology*, May 1996, pp. 97-108, vol. 22, No. 1, Blackwell Science Ltd., Oxford, UK.

Tart, Anne H. et al., "The Alternative Sigma Factor AlgT Represses *Pseudomonas aeruginosa* Flagellum Biosynthesis by Inhibiting Expression of fleQ", *Journal of Bacteriology*, Dec. 2005, pp. 7955-7962, vol. 187, No. 23, American Society for Microbiology, Washington, D.C.

Jain, Sumita et al., "Role of an Alginate Lyase for Alginate Transport in Mucoid *Pseudomonas aeruginosa*", *Infection and Immunity*, Oct. 2005, pp. 6429-6436, vol. 73, No. 10, American Society for Microbiology, Washington, D.C.

(56) References Cited

OTHER PUBLICATIONS

Franklin, Michael J. et al., "Evidence that the algI/algJ Gene Cassette, Required for O Acetylation of *Pseudomonas aeruginosa* Alginate, Evolved by Lateral Gene Transfer", *Journal of Bacteriology*, Jul. 2004, pp. 4759-4773, vol. 186, No. 14, American Society for Microbiology, Washington, D.C.

Firoved, Aaron M. et al., "Microarray Analysis of Global Gene Expression in Mucoid *Pseudomonas aeruginosa*", *Journal of Bacteriology*, Feb. 2003, pp. 1071-1081, vol. 185, No. 3, American Society for Microbiology, Washington, D.C.

Schurr, M.J. et al., "Multiple Promoters and Induction by Heat Shock of the Gene Encoding the Alternative Sigma Factor AlgU ($\alpha^E$) Which Controls Mucoidy in Cystic Fibrosis Isolates of *Pseudomonas aeruginosa*", *Journal of Bacteriology*, Oct. 1995, pp. 5670-5679, vol. 177, No. 19, American Society for Microbiology, Washington, D.C.

Hoang, Tung T. et al., "Integration-Proficient Plasmids for *Pseudomonas aeruginosa*: Site-Specific Integration and Use for Engineering of Reporter and Expression Strains", *Plasmid*, 2000, pp. 59-72, vol. 43, Academic Press, Amsterdam, Netherlands.

Fyfe, J.A.M. et al., "Synthesis, Regulation and Biological Function of Bacterial Alginate", *Progress in Industrial Microbiology*, 1983, pp. 45-83, vol. 18, Elsevier Science Publishers B.V., Amsterdam, The Netherlands.

Miller, Jeffrey H., "Experiment 48: Assay of β-Galactosidase", *Experiments in Molecular Genetics*, 1972, pp. 352-355, Cold Spring Harbor Laboratory, Cold Spring Harbor, New York, USA.

Pedersen, Svend Stenvang et al., "Purification, Characterization, and Immunological Cross-Reactivity of Alginates Produced by Mucoid *Pseudomonas aeruginosa* from Patients with Cystic Fibrosis", *Journal of Clinical Microbiology*, Apr. 1989, pp. 691-699, vol. 27, No. 4, American Society for Microbiology, Washington, D.C.

Ott, C. Mark et al., "Bacterial Alginate: An Alternative Industrial Polymer", *Trends in Polymer Science*, 1995, pp. 402-406, vol. 3, No. 12, Elsevier, Cambridge, Royaume-Uni.

Rehm, B.H.A et al., "Bacterial alginates: biosynthesis and applications", *Applied Microbiology Biotechnology*, Sep. 1997, pp. 281-288, vol. 48, No. 3, Springer-Verlag, Berlin, Allemagne.

Gibson, Ronald L., "Pathophysiology and Management of Pulmonary Infections in Cystic Fibrosis", *American Journal of Respiratory and Critical Care Medicine*, Oct. 15, 2003, pp. 918-951, vol. 168, No. 8, American Thoracic Society, Washington, D.C.

Wozniak, Daniel J., "Effects of Subinhibitory Concentrations of Macrolide Antibiotics on *Pseudomonas aeruginosa*", *Chest*, Feb. 2004, pp. 62S-69S, vol. 125, No. 2, American College of Chest, Northbrook, IL.

Miller, Melissa B. et al., "Laboratory Aspects of Management of Chronic Pulmonary Infections in Patients with Cystic Fibrosis", *Journal of Clinical Microbiology*, Sep. 2003, pp. 4009-4015, vol. 41, No. 9, American Society for Microbiology, Washington, D.C.

Stover, C.K. et al., "Complete genome sequence of *Pseudomonas aeruginosa* PA01, an opportunistic pathogen", *Nature*, Aug. 31, 2000, vol. 406, pp. 959-964, Nature Publishing, London, Royaume-Uni.

Malhotra, Sonal et al., "Proteome Analysis of the Effect of Mucoid Conversion on Global Protein Expression in *Pseudomonas aeruginosa* Strain PAO1 Shows Induction of the Disulfide Bond Isomerase, DsbA", *Journal of Bacteriology*, Dec. 2000, pp. 6999-7006, vol. 182, No. 24, American Society of Microbiology, Washington, DC.

International Search Report mailed Aug. 13, 2009 for International Application No. PCT/US09/02605, 4 pgs, ISA, Alexandria, Virginia.

* cited by examiner

STABLE BACTERIAL CULTURES FOR PRODUCING ALGINATES

CROSS REFERENCE TO RELATED APPLICATIONS

This application claims the benefit of the filing date of U.S. Provisional Patent Application No. 61/048,858, filed Apr. 29, 2008, which is incorporated herein by reference in its entirety.

STATEMENT REGARDING FEDERALLY-SPONSORED RESEARCH AND DEVELOPMENT

Statement under MPEP 310. The U.S. government and the West Virginia State government have a paid-up license in this invention and the right in limited circumstances to require the patent owner to license others on reasonable terms as provided for by the terms of NNA04CC74G awarded by the National Aeronautics and Space Administration (NASA) and the research grants awarded by the NASA West Virginia Space Grant Consortium.

Part of the work performed during development of this invention utilized U.S. Government and the State West Virginia funds. The U.S. Government and West Virginia government have certain rights in this invention.

REFERENCE TO A SEQUENCE LISTING SUBMITTED ELECTRONICALLY VIA EFS-WEB

The content of the electronically submitted sequence listing (Name: sequence listings.ascii.txt, Size: 10 kilobytes; and Date of Creation: Aug. 4, 2009) filed with the application is incorporated by reference in its entirety.

BACKGROUND OF THE INVENTION

1. Field of the Invention

The present invention relates to methods for alginate production using mucoid bacterial cultures. The present invention also provides for pharmaceutical compositions that contain bacterial alginate. The bacterial alginate may be produced using genetically engineered bacteria.

2. Background Art

Alginate

Alginates are salts of alginic acid, which is a linear heteropolysaccharide. Alginates are comprised of two subunits, β-D-mannuronic acid (denoted M units) and α-L-guluronic acid (denoted G units). Alginates may be found in and isolated from various species, in particular from algae belonging to the order Phaeophyceae and soil bacteria such as *Azotobacter vinelandii* and *Azotobacter crococcum*. Common algal sources of alginates include *Laminaria digitata, Ecklonia maxima, Macrocystis pyrifera, Lessonia nigrescens, Ascophyllum nodosum, Laminaria japonica, Durvillea antartica, Durvillea potatorum* and *Laminaria hyperborea*.

Alginates produced from various sources differ considerably in their structure. For example, alginates produced by seaweed are generally not acetylated, whereas bacteria produce alginates with a higher degree of acetylation. In addition, the molecular weight and the ratio of β-D-mannuronic acid and α-L-guluronic acid units in alginates can vary based on the alginate source and the conditions in which the alginate is produced. These structural differences can result in changes in alginate properties.

Alginates are commonly purified from brown seaweeds. However, brown seaweed is a limited resource and extraction of alginate results in destruction of this precious resource. In addition, there are several problems associated with seaweed alginate. First, their harvest is seasonal and alginate production is dependent on cold ocean temperature, which is rising, most likely due to global warming. Second, extraction of seaweed alginate involves as many as 15-20 different processing steps. Third, the composition of the alginate produced by the seaweed is fixed and cannot be altered to produce a better or different product to expand commercial applications.

Alginate can be used in a wide variety of products. For example, seaweed alginates are used in food, dental and cosmetic products. The alginates are particularly useful as gelling, thickening, stabilizing, swelling and viscosity imparting agents. Seaweed alginate is used in the textile and paper industries and also serves as a thickening agent in common food items, such as ice cream, salad dressing, pet food chunks, low fat spreads, sauces and pie filings. Seaweed alginate is also incorporated into wound dressings to provide a moist surface for healing. Alginate fibers trapped in a wound are readily biodegraded. Dressings with seaweed alginate are used to treat ulcers in diabetic patients. Propylene glycol alginate has been used as an acid-stable stabilizer for uses such as preserving the white fluffy head of foam on beers. Seaweed alginate absorbs radioactive elements, heavy metals and free radicals. Because alginate cannot be broken down by bile or saliva and cannot be absorbed by the body, it is secreted from the body together with the heavy metals and radioactive substances. The ever-increasing applications of this biopolymer have led to continued interest in better understanding the biosynthesis pathway and regulatory mechanisms as well as optimization of microbial production process.

Regulation of Alginate Production Pathway in *Pseudomonas*

Synthesis of alginate and its regulation has been the object of numerous studies (Govan, J. R., and V. Deretic, *Microbiol. Rev.* 60:539-74 (1996); Ramsey, D. M., and D. J. Wozniak, *Mol. Microbiol.* 56:309-22 (2005)). Alginate production is positively and negatively regulated in wild-type cells of *Pseudomonas*.

Three tightly linked genes algU, mucA, and mucB have been identified with a chromosomal region shown by genetic means to represent the site where mutations cause conversion to mucoidy (see U.S. Pat. Nos. 6,426,187, 6,083,691, 5,591,838, and 5,573,910, incorporated herein by reference in their entireties).

Positive regulation centers on the activation of the alginate biosynthetic operon (Govan, J. R., and V. Deretic, *Microbiol. Rev.* 60:539-74 (1996)). Positive regulators include the alternative stress-related sigma factor AlgU (Martin, D. W., et al., *Proc. Natl. Acad. Sci.* 90:8377-81 (1993)), also called AlgT (DeVries, C. A., and D. E. Ohman, *J. Bacteriol.* 176:6677-87 (1994)), and transcriptional activators AlgR and AlgB, which belong to a bacterial two component signaling system. The cognate kinase of AlgB is KinB (Ma, S., et al., *J. Biol. Chem.* 272:17952-60 (1997)) while AlgZ (Yu, H., et al., *J. Bacteriol.* 179:187-93 (1997)) may be the kinase that phosphorylates AlgR. However, unlike a typical two-component system, alginate overproduction is independent of phosphorylation of AlgR or AlgB (Ma, S., et al., *J. Bacteriol.* 180:956-68 (1998)).

Negative regulation of alginate has focused on the post-translational control of AlgU activity. In alginate regulation, the master regulator is AlgU and the signal transducer is MucA, a trans-inner membrane protein whose amino terminus interacts with AlgU to antagonize the activity of AlgU, and the carboxyl terminus with MucB, another negative regulator of alginate biosynthesis. The algUmucABC cluster is conserved among many Gram-negative bacteria. AlgU belongs to the family of extracytoplasmic function (ECF) sigma factors that regulate cellular functions in response to extreme stress stimuli. The action of ECF sigma factors is negatively controlled by MucA, MucB and MucC. This set of proteins forms a signal transduction system that senses and responds to envelope stress.

MucA is the anti-sigma factor that binds AlgU and antagonizes its transcriptional activator activity (Schurr, M. J., et al., *J. Bacteriol.* 178:4997-5004 (1996)). Consequently, inactivation of mucA in *P. aeruginosa* strain PAO1 results in the mucoid phenotype (Alg+) (Martin, D. W., et al., *Proc. Natl. Acad. Sci. USA* 90:8377-81 (1993); Mathee, K., et al., *Microbiology* 145:1349-57 (1999)). Clinical mucoid isolates of *P. aeruginosa* carry recessive mutations in mucA (Anthony, M., et al., *J. Clin. Microbiol.* 40:2772-8 (2002); Boucher, J. C., et al., *Infect. Immun.* 65:3838-46 (1997)). The transition from a non-mucoid to mucoid variant occurs in concurrence with the mucA22 allele after exposure to hydrogen peroxide, an oxidant in neutrophils (Mathee, K., et al., *Microbiology* 145: 1349-57 (1999)).

MucB is located in the periplasm in association with the periplasmic portion of MucA (Mathee, K., et al., *J. Bacteriol.* 179:3711-20 (1997); Rowen, D. W., and V. Deretic, *Mol. Microbiol.* 36:314-27 (2000)). MucC is a mild negative regulator whose action is not completely understood, but thought to be in synergy with MucA and/or MucB (Boucher, J. C., et al., *Microbiology* 143:3473-80 (1997)). MucD is a negative regulator whose dual functions include periplasmic serine protease and chaperone activities that are thought to help remove misfolded proteins of the cell envelope for quality control (Boucher, J. C., et al., *J. Bacteriol.* 178:511-23 (1996); Yorgey, P., et al., *Mol. Microbiol.* 41:1063-76 (2001)).

Alginate Production in *Pseudomonas*

Alginate production in mucoid strains of *P. aeruginosa* has been limited because these strains quickly convert to non-mucoid strains and do not produce sufficient amounts of alginate for commercial application. Other species of *Pseudomonas* generally produce small amounts of alginates, or alginates of low molecular weight. In spontaneous alginate-producers, non-mucoid revertants tend to arise frequently (Flynn and Ohman, *J. Bacteriol.* 170:1452-1460 (1988)).

Non-pathogenic species of *Pseudomonas* such as *P. putida*, *P. mendocina* and *P. fluorescens* produce exopolysaccharides similar to acetylated alginates. (Govan J. R. W. et al., *J. of General Microbiology* 125:217-220 (1981)). Conti et al. also describe production of alginates from *P. fluorescens* and *P. putida*. (Conti, E. et al., *Microbiology* 140:1125-1132 (1994)). However, these strains produce small quantities of alginate.

There is therefore a need for suitable bacterial sources and methods for inexpensive mass production of alginate. In particular, there is a need for bacterial sources producing large amounts of high quality alginate with defined structure and desired molecular weight.

BRIEF SUMMARY OF THE INVENTION

The present invention describes methods of alginate production in mucoid bacteria, biological cultures for alginate production, and compositions that contain alginate produced by mucoid bacteria. Bacterial alginates are also described.

In one embodiment of the invention, the invention provides a method for producing alginate comprising culturing mucoid bacteria and isolating alginate, wherein the mucoid bacteria have increased MucE activity.

The present invention is also directed to methods for producing alginate comprising culturing mucoid bacteria and isolating alginate, wherein the mucoid bacteria have decreased MucA activity. In some embodiments, the decreased MucA activity is the result of a transposon insertion. In some embodiments, the transposon insertion is upstream of the mucA coding sequence. In some embodiments, the decreased MucA activity is the result of a mutation that results in a truncated MucA protein.

The present invention is also directed to a method for producing alginate comprising culturing mucoid bacteria and isolating alginate, wherein the mucoid bacteria have increased ClpP, ClpP2 and/or ClpX protease activity.

The present invention is also directed to a method for producing alginate comprising culturing mucoid bacteria and isolating alginate, wherein the mucoid bacteria have decreased MucD activity.

The present invention is further directed to a method for producing alginate comprising culturing mucoid bacteria and isolating alginate, wherein the mucoid bacteria are stable for at least two weeks.

The present invention is also directed to a method for producing alginate comprising culturing mucoid bacteria and isolating alginate, wherein the mucoid bacteria do not express at least one endotoxin gene.

Additionally, the present invention is directed to a biological culture comprising stable mucoid bacteria that produce alginate wherein the bacteria have increased MucE activity. In some embodiments, the biological culture comprises stable mucoid bacteria that produce alginate wherein the bacteria have increased ClpP, ClpP2 and/or ClpX protease activity. In some embodiments, the biological culture comprises stable mucoid bacteria that produce alginate wherein the bacteria have decreased MucA activity. In some embodiments, the invention is directed to a biological culture comprising stable mucoid bacteria that produce alginate wherein the bacteria are stable for at least two weeks. In some embodiments, the biological culture comprises stable mucoid bacteria that produce alginate wherein the bacteria do not express at least one endotoxin gene.

The present invention is also directed to a composition comprising alginate wherein the alginate is produced by a stable bacterial culture that has increased MucE activity. In some embodiments, the invention is directed to a composition comprising alginate wherein the alginate is produced by a stable bacterial culture that has increased ClpP, ClpP2, and/or ClpX activity. In some embodiments, the composition comprises alginate wherein the alginate is produced by a stable bacterial culture that has decreased MucA activity. In some embodiments, the composition comprises alginate wherein the alginate is produced by a bacterial culture that is stable for at least two weeks. In some embodiments, the composition comprises alginate wherein the alginate is produced by a stable bacterial culture that does not express at least one endogenous endotoxin gene. In some embodiments, the alginate in the composition is at least 90% pure.

In some embodiments of the present invention, the stable mucoid bacteria is *P. aeruginosa*. In some embodiments of the present invention, the *P. aeruginosa* are cultured at 37° C. In some embodiments of the present invention, the alginate is acylated and the degree of acetylation is about 0.1 to 1.0. In some embodiments, the ratio of M blocks to G blocks in the alginate is between about 1:10 to 10:1. In some embodiments, the alginate has a molecular weight of between about 500 and 20,000 kD. In some embodiments, the alginate has a viscosity between about 10 and 500 dL/g. In some embodiments, the alginate has a hydrodynamic radius between about 50 and 500 nm.

BRIEF DESCRIPTION OF THE DRAWINGS/FIGURES

The following drawings form part of the present specification and are included to further demonstrate certain aspects of the present invention. The invention may be better understood by reference to one or more of these drawings in combination with the detailed description of specific embodiments presented herein.

FIG. 1 shows a schematic diagram depicting the transposition by the himar1 mariner transposon of pF AC in Pseudomonas aeruginosa nonmucoid reference strain PAO1 (FIG. 1A) and schematics showing three genetic clusters that regulate the mucoid phenotype identified via the himar1 mariner transposon mutagenesis in wild-type PAO1 (FIG. 1B-D). In FIG. 1A, the 5'TA3' dinucleotide on the chromosome is underlined, and the following abbreviations are used: IR, inverted repeat; $Gm^R$, the gentamicin resistance marker (aacC1); $P_{Gm}$, the $\sigma^{70}$ dependent promoter of aacC1. GM5OUT and GM3OUT are DNA primers specifically designed for inverse PCR (iPCR). Restriction digestion sites that can be used for iPCR are denoted: K, Kpn I; S, Sal I; H, Hind III; E, EcoR I; P, Pst I; and Sm, Sma I. The nucleic acid sequences of the 5'TA3' dinucleotide and inverted repeat regions of the himar1 mariner transposon are provided in SEQ ID NOS: 11 and 12, respectively. FIGS. 1B, 1C and 1D show the algU mucABCD, the mucE, and the algB kinB regions respectively. Open circles represent the sites of transposon insertions. The arrows indicate the directions of transcription driven by the transposon-derived promoter ($P_{Gm}$). The numbers below the gene represent the corresponding positions on the annotated PAO1 genome. Designations of VE, V and DR refer to the mucoid mutants generated in the backgrounds of PAO1, PAO57NM and PA14, respectively.

FIG. 2 shows alginate production by an algU strain, mucABCD strains and wild-type P. aeruginosa PAO1. Amounts of alginate (μg alginate/mg protein) were measured from 4-72 hours. Asterisk indicates significant differences at P<0.05 in comparison with the same time point in wild-type PAO1 (t test). The genotype of each mutant is shown. The +oe superscript used in panel B refers to the overexpression of the algU-mucABC operon. Bacterial cells were grown on PIA plates and incubated at 37° C. for 4-72 hours.

Figure 5:
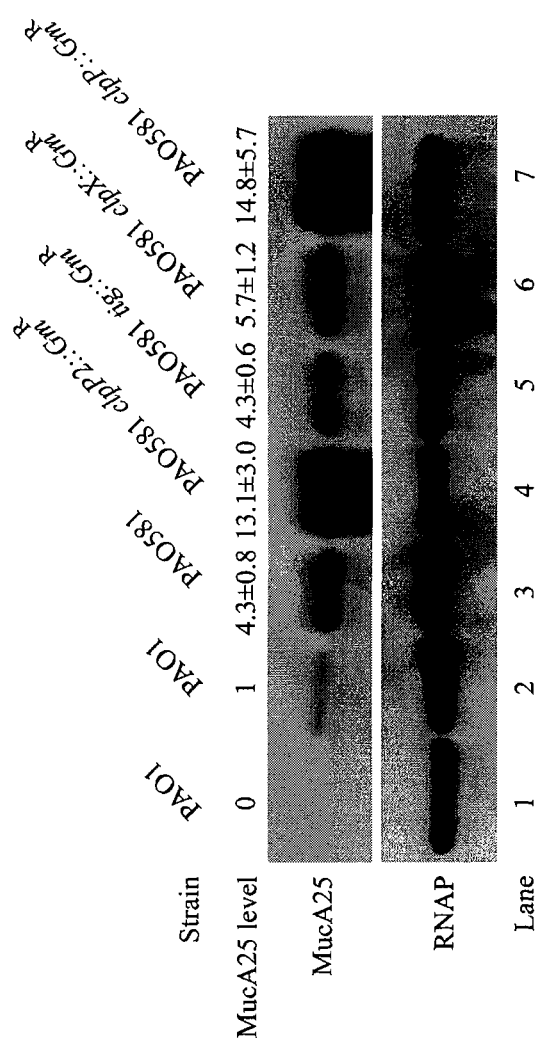

FIG. 5 shows western blot analysis of N-terminal HA-tagged MucA25 protein in P. aeruginosa. Lane 1: PAO1/pUCP20T-pBAD (vector control). Lanes 2-7: HA-MucA25 was expressed from pUCP20T-$P_{BAD}$-mucA25 under the induction of 0.05% arabinose. Rabbit polyclonal antibody against the P. aeruginosa RNA polymerase α-subunit (RNAP) was used as a loading control.

Figure 6:
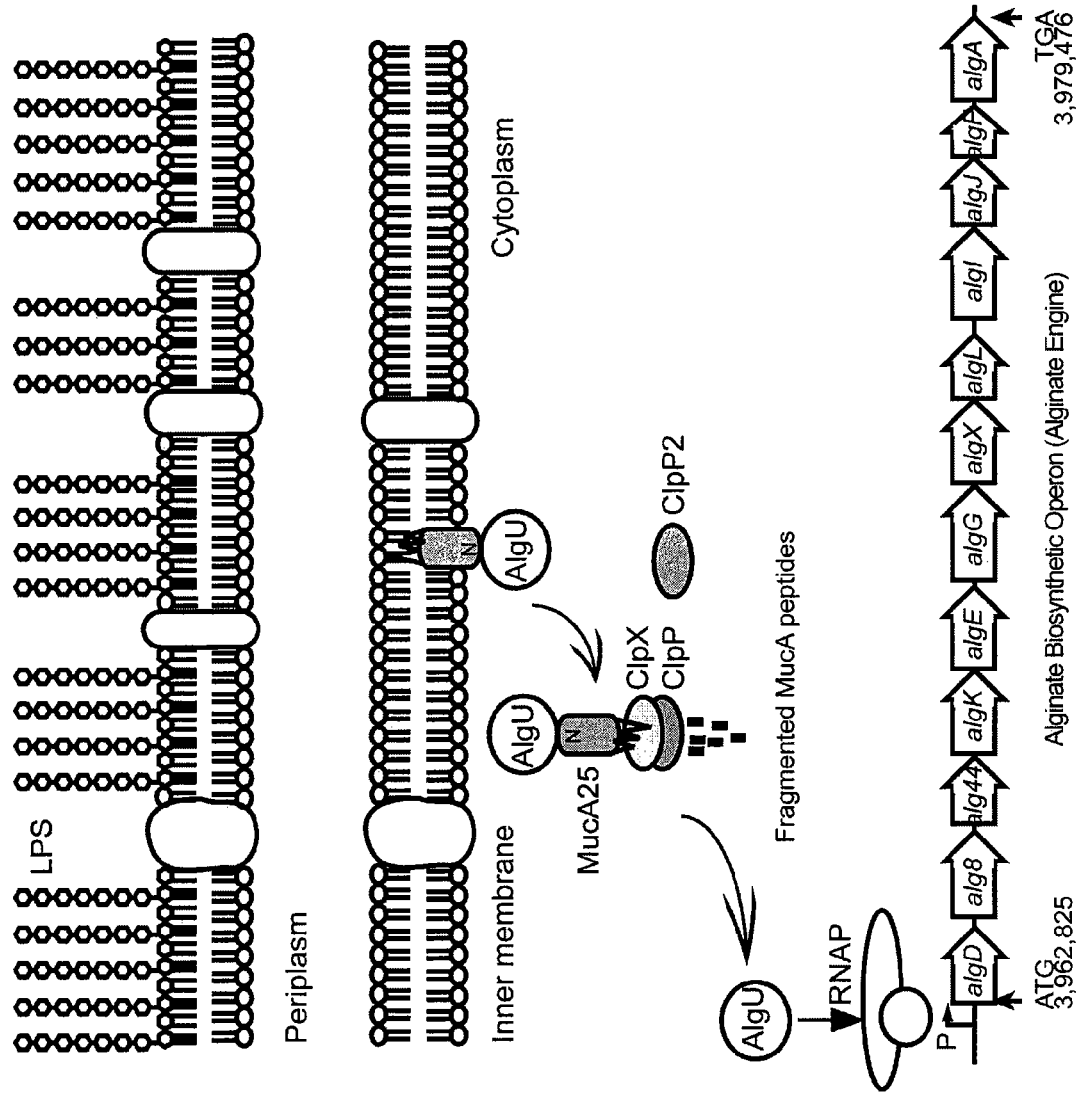

FIG. 6 shows a schematic diagram for the mucA25 mutation-caused mucoid phenotype in P. aeruginosa PAO581 and the cytoplasmic proteolysis involved in the regulation of alginate biosynthesis. The single base deletion of T180 resulted in a premature stop codon in mucA and C-terminal truncation of MucA to MucA25. This truncation is before the transmembrane domain (84-104) of wt MucA but the cellular localization of MucA25 has yet to be proven. The truncated N-terminus of MucA25 is subjected to proteolysis by ClpXP and ClpP2, leading to the release of the sequestered AlgU to drive transcription of the alginate biosynthesis operon of algD-A.

Figure 7:
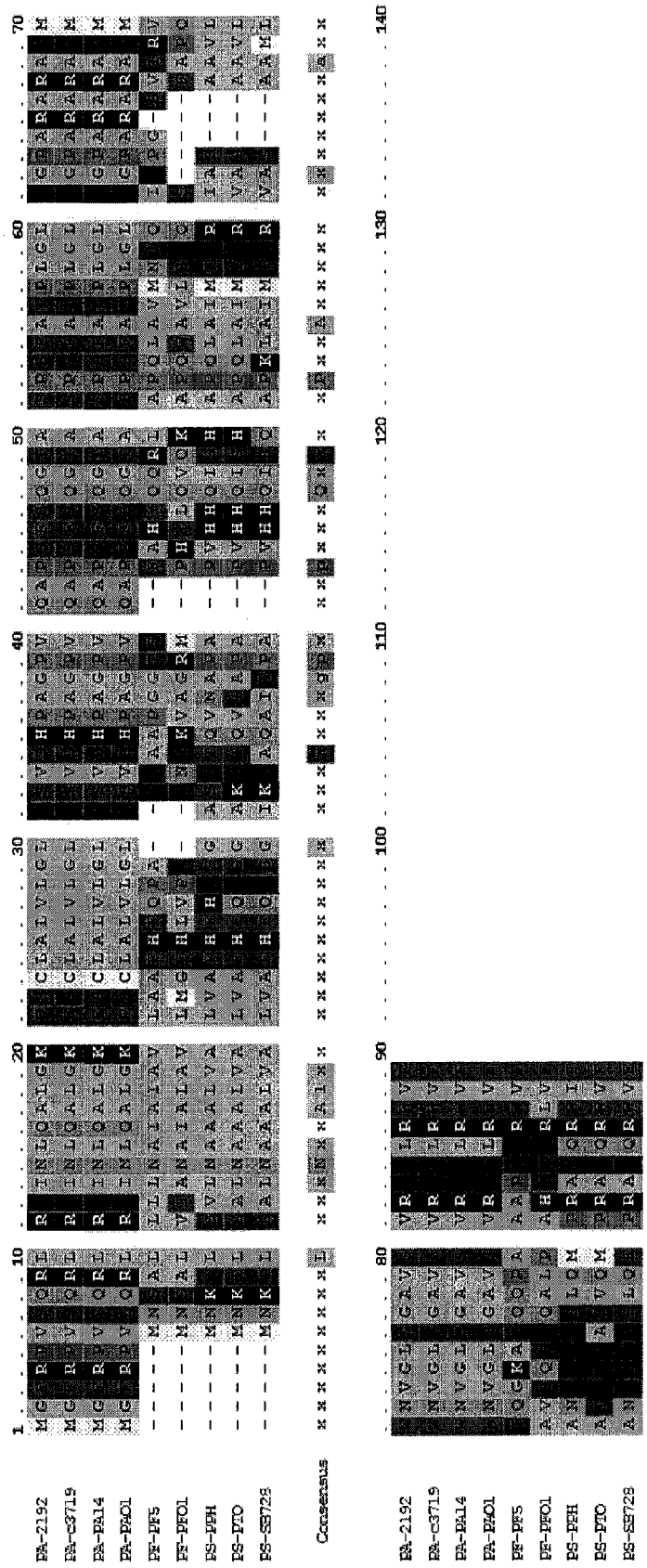

FIG. 7 shows an alignment of the mucE homologs identified from the completed and partially completed genomes of three species within the genus of Pseudomonas. The three species are PA: Pseudomonas aeruginosa; PF: Pseudomonas fluorescens; and PS: Pseudomonas syringae. The strains shown are: PA-PAO1 (SEQ ID NO: 4), Pseudomonas aeruginosa PAO1 (causes opportunistic infections in humans); PA-PA14 (SEQ ID NO: 3), Pseudomonas aeruginosa UCBPP PA14 (human clinical isolate); PA-2192 (SEQ ID NO: 1), Pseudomonas aeruginosa 2192 (CF patient isolate); PA-C3719 (SEQ ID NO: 2), Pseudomonas aeruginosa C3719 (unknown source but probably clinical origin); PS-PPH (SEQ ID NO: 7), Pseudomonas syringae pv. phaseolicola 1448A (causes halo blight on beans); PS-PTO (SEQ ID NO: 8), Pseudomonas syringae pv. tomato DC3000 (bacterial speck disease on tomato plants); PS-SB728 (SEQ ID NO: 9), Pseudomonas syringae pv. syringae B728a (brown spot disease on beans); PF-PF5 (SEQ ID NO: 5), Pseudomonas fluorescens Pf-5 (Saprophyte) (the production of a number of antibiotics as well as the production of siderophores by this strain can inhibit phytopathogen growth); and PF-PFO1 (SEQ ID NO: 6), Pseudomonas fluorescens NO-1 (microorganism of putrefaction and well adapted to soil environments). SEQ ID NO: 10 provides the mucE consensus sequence for Pseudomonas.

Figure 8:

FIG. 8 shows colony morphologies on a PIA plate after growth at 37° C. for 24 hours of the reference strain of P. aeruginosa PAO1, mucoid variant PAO581 (PAO1 mucA25), and null mutants of tig (PAO581DR23), clpP (PAO581DR58), clpX (PAO581DR45) and clpP2 (PAO581DR3).

Figure 9:
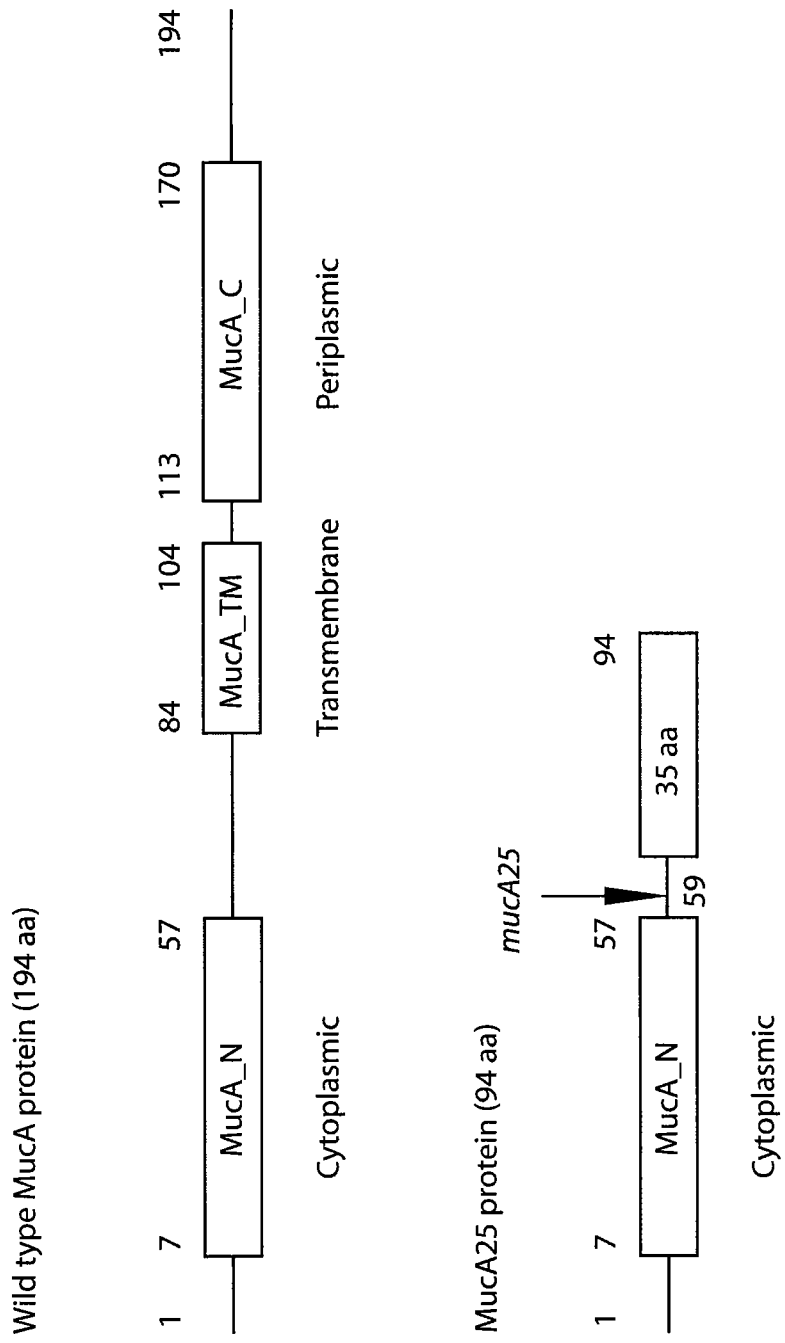

FIG. 9 shows a schematic of wild-type and mutant MucA proteins.

Figure 10:
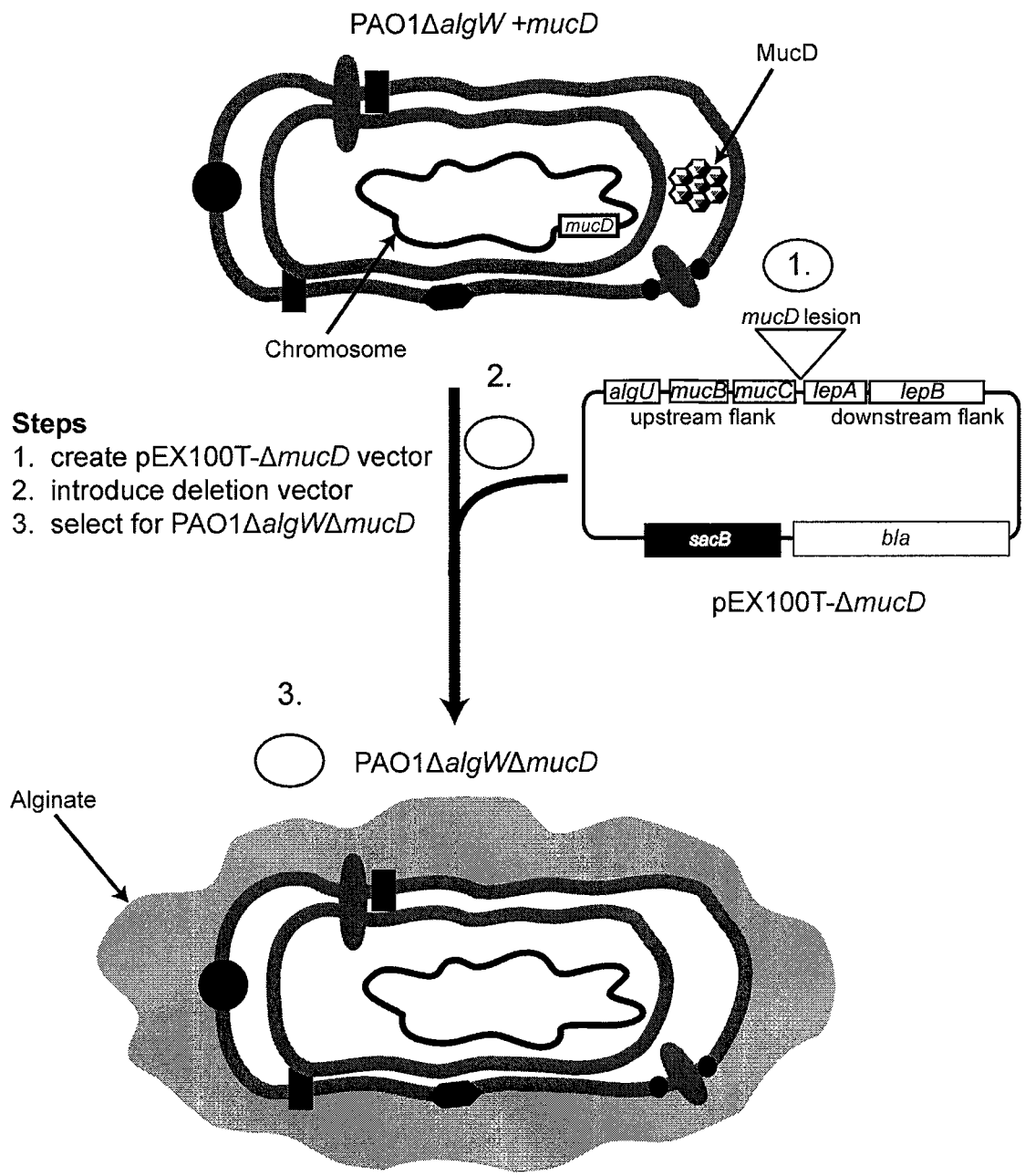

FIG. 10 shows the genetic construction of the alginate producing strain HD101.

DETAILED DESCRIPTION OF THE INVENTION

Definitions

The term "positive regulator" as used herein, means that the induction of expression and/or activity of a gene encoding a functional protein causes alginate overproduction. Examples of positive regulators include algU, mucE, and algW.

The term "negative regulator" as used herein, means that the absence of such a gene encoding a functional protein causes alginate overproduction. Examples of negative regulators include kinB, mucA, mucB, and mucD.

The term "recombinant," as used herein, means that a protein is derived from recombinant (e.g., microbial) expression systems. The term "microbial" refers to recombinant proteins made in bacterial or fungal (e.g., yeast) expression systems. As a product, the term "recombinant microbial" defines a protein produced in a microbial expression system which is essentially free of native endogenous substances (e.g., glycan). Protein expressed in most bacterial cultures, e.g., E. coli, will be free of glycan.

The term "DNA sequence" refers to a DNA polymer, in the form of a separate fragment or as a component of a larger DNA construct. Preferably, the DNA sequences are in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences. Genomic DNA containing the relevant sequences could also be used. Sequences of nontranslated DNA may be present 5' or 3' from the open reading frame, where the same do not interfere with manipulation or expression of the coding regions.

The term "nucleotide sequence" refers to a heteropolymer of deoxyribonucleotides. DNA sequences encoding the proteins of this invention can be assembled from fragments and short oligonucleotide linkers, or from a series of oligonucleotides, to provide a synthetic gene which is capable of being expressed in a recombinant transcriptional unit.

The term "recombinant expression vector" refers to a replicable DNA construct used either to amplify or to express DNA which encodes the recombinant proteins of the present invention and which includes a transcriptional unit comprising an assembly of (1) a genetic element or elements having a regulatory role in gene expression, for example, promoters or enhancers, (2) a structure or coding sequence which is transcribed into mRNA and translated into protein, and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

As used herein, the term "expression vector" refers to a construct made up of genetic material (i.e., nucleic acids). Typically, a expression vector contains an origin of replication which is functional in bacterial host cells, e.g., *Escherichia coli*, and selectable markers for detecting bacterial host cells comprising the expression vector. Expression vectors of the present invention contain a promoter sequence and include genetic elements as described herein arranged such that an inserted coding sequence can be transcribed and translated in prokaryotes or eukaroytes. In certain embodiments described herein, an expression vector is a closed circular DNA molecule. The term "plasmid" is used interchangeably with "expression vector."

The term "expression" refers to the biological production of a product encoded by a coding sequence. In most cases, a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product. The term "overexpress" or "overexpression" refers to a biological product that is transcribed or translated at a rate higher, is more stable than that in wild-type strains and/or is more active than that in wild-type strains.

The term "recombinant microbial expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

As used herein, the term "biological functional equivalent" refers to proteins which contain modifications or changes in the structure of the coding region, but still result in a protein molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in the DNA coding sequence and nevertheless obtain a protein with like or even counterveiling properties (e.g., antagonistic v. agonistic). It is thus contemplated by the inventors that various changes may be made in the DNA sequence of proteins or peptides without appreciable loss of their biological utility or activity.

As used herein, the term "comprising" means including the steps or elements that are identified following that term, but any such steps or elements are not exhaustive, and an embodiment may include other steps or elements.

Alginate

Alginates are comprised of two subunits: β-D-mannuronic acid (denoted M units) and α-L-guluronic acid (denoted G units). Alginic acid and alginates of the present invention may comprise homopolymeric sequences of mannuronic acid, known as M blocks, homopolymeric sequences of guluronic acid, known as G blocks, and mixed sequences of mannuronic acid and guluronic acid units, known as MG blocks or alternating blocks. Alginate of the present invention may contain the following structure of an alginate chain. The structure includes an M block, a G block and an MG block followed by a G block:

Alginates of the present invention may contain all three different blocks and each block may contain from about three to about twenty monomer (M or G) units. The distribution of the M, G and MG blocks and also the relative quantity of the M and G units can vary. The ratio of M and G units and/or blocks can vary depending on the growth conditions and bacterial strain used. High ratios of M block to G block result in highly viscous solutions.

In some embodiments of the present invention, the alginate can have a particular ratio of M blocks to G blocks. For example, the ratio of M blocks to G blocks can be between 1:10 or 10:1. Alginate with a ratio of M blocks to G blocks of between 1:10 and 1:1 and alginate with a ratio of M blocks to G blocks of between 1:1 and 1:10 are also contemplated. In some embodiments, the ratio of M blocks to G blocks is about 2:1, 3:1, 4:1 or about 5:1. In some embodiments, the ratio of M blocks to G blocks is between 2:1 and 3:1, between 3:1 and 4:1 or between 4:1 and 5:1.

In other embodiments of the invention, the alginate can have a particular percentage of M and G units. In some embodiments, the alginate contains at least 50% M units, at least 60% M units, at least 70% M units, at least 80% M units, at least 90% M units, or at least 95% M units. In other embodiments of the invention, the alginate has between 50 and 60% M units, between 60 and 70% M units, between 70 and 80% M units or between 80 and 90% M units. In some embodiments, the alginate contains at least 50% G units, at least 60% G units, at least 70% G units, at least 80% G units, at least 90% G units, or at least 95% G units. In other embodiments of the invention, the alginate has between 50 and 60% G units, between 60 and 70% G units, between 70 and 80% G units or between 80 and 90% G units.

The M/G ratio can be determined using any method known in the art. For example, the M/G ratio can be determined using the crude carbazole analysis on the content of uronic acid with D-mannuronic acid lactone as the standard (Knutson, C. A., and A. Jeanes, *Anal. Biochem.* 24:470-481 (1968)). This ratio can also be more precisely determined with a high-performance liquid chromatographic (HPLC) method as described in Sanchez-Machado, D. I., et al., *Biomed Chromatogr.* 18:90-97 (2004)).

Molecular weight is another characteristic of alginate. As the polymeric chain increases in length and therefore increases in molecular weight, the alginate becomes less elastic. High molecular weight alginate results in increased viscosity. The molecular weight can vary based on how the alginate is produced and/or purified. The molecular weight of alginate purified from seaweed varies, but is generally between 70 and 80 kD. In contrast, the molecular weight of alginate produced from bacteria is generally about 500 kD.

In some embodiments of the present invention, the alginate has a particular molecular weight. For example, in some embodiments, the alginate has an average molecular weight of about 500 kD, 600 kD, 700 kD, 800 kD, 900 kD, 1000 kD, 5000 kD, 10,000 kD or about 15,000 kD. In some embodiments of the invention, the average molecular weight of the alginate is between about 500 and 1000 kD, 1000 and 10,000 kD, 10,000 and 20,000 kD, 10,0000 and 15,0000 kD or between about 15,000 and 20,000 kD. In some embodiments of the invention, the average molecular weight of the alginate is between about 500 and 10,000 kD, 500 and 20,000 kD, 500 and 15,0000 kD or between about 500 and 20,000 kD.

The molecular weight of the alginate can be determined using any method known in the art. For example, molecular weight can be determined using art-known technologies and technologies including, but not limited to, Gel Permeation Chromatography (GPC), Flow Injection Polymer Analysis (FIPA), Dilute Solution Viscosity (DSV) and Dynamic Light Scattering (DLS). The molecular weight can also be determined, for example, by using the Viscotek Triple Detector System (Houston, Tex.), which utilizes multiple technologies including the intrinsic viscosity (dL/g; essentially the inverse density) and Low Angle Light Scattering to measure polymers with large molecular weights, such as 10 million Dalton. While older technologies utilizing multi-angle light scattering detectors (using a lowest usable angle of about 35 degrees) can introduce an error of 60%, Viscotek's Low Angle Light Scattering detector introduces an approximate 2% error rate in molecular weight calculation, thus allowing for a more precise determination of the molecular weight of bacterial alginate.

Acetylation, i.e. the addition of acetyl groups, can also affect the properties of alginates and varies based on methods of production and purification used. Bacterially produced alginates may be O-acetylated on the C-2 and C-3 carbons of mannuronic acid residues, and the degree of acetylation may vary. The degree of acetylation is generally expressed as the number of acetyl groups per monomer. For example, a degree of acetylation of 0.5 indicates an average of 1 acetyl group per 2 monomers. In some embodiments of the invention, the alginate has a particular degree of acetylation. For example, in some embodiments, the degree of acetylation is about 0.1, about 0.2, about 0.3, about 0.4, about 0.5, about 0.6, about 0.7, about 0.8, about 0.9, about 1.0, or about 2.0. In other embodiments of the invention, the degree of acetylation is between about 0.1 and 0.3, 0.3 and 0.5, 0.5 and 0.7, 0.7 and 0.9 or between about 0.9 and 1.0.

The properties of alginate can also be affected by its hydrodynamic radius. The hydrodynamic radius is the radius as calculated by the diffusional properties of the particles. It is indicative of the apparent size of the particle. In some embodiments of the invention, the alginate has a particular hydrodynamic radius. For example, the hydrodynamic radius can be about 10 nm, about 50 nm, about 100 nm, about 150 nm, about 200 nm, about 250 nm or about 300 nm. In some embodiments of the invention, the hydrodynamic radius is between about 50 and 500 nm, 100 and 500 nm, 200 and 500 nm, 100 and 400 nm, 200 and 400 nm or between about 250 and 350 nm. The hydrodynamic radius can also be between about 50 and 100 nm, 50 and 150 nm, 50 and 200 nm, 50 and 250 nm, 50 and 300 nm, 50 and 400 nm, 50 and 500 nm or between about 50-1000 nm. The hydrodynamic radius can be measured using any technique known in the art, including for example, by dynamic light scattering.

Another feature of alginate is its viscosity. Viscosity is affected by, for example, a combination of molecular weight, M:G ratios and/or acetylation. In some embodiments of the present invention, the alginate has a particular viscosity. For example, in some embodiments, the viscosity is about 5 dL/g, about 10 dL/g, greater than 20 dL/g, about 30 dL/g, about 40 dL/g, about 50 dL/g, about 60 dL/g, about 70 dL/g, about 80 dL/g, about 90 dL/g, about 95 dL/g, about 96 dL/g, about 97 dL/g, or about 98 dL/g. In some embodiments, the viscosity is between about 10 and 500 dL/g, 25 and 250 dL/g, 50 and 200 dL/g, 75 and 150 dL/g, 80 and 125 dL/g, 90 and 110 dL/g, 95 and 105 dL/g, 96 and 98 dL/g or between about 95 and 100 dL/g. Viscosity can be measured using any method known in the art. For example, viscosity can be measured as the intrinsic viscosity (IV) using Viscotek Corp. technologies. IV is defined as a direct measurement of the amount of volume occupied by a gram of fully solvated molecules in solution, which essentially describes the molecular size of bacterial alginates in solution.

The amount of alginate produced by the strains of the present invention is as high as about 100 g per liter of broth (g/L), 90 g/L, 80 g/L, 70 g/L, 60 g/L, 50 g/L, 40 g/L, 30 g/L, 20 g/L, 18 g/L, 16 g/L, 14 g/L, 12 g/L, 10 g/L, 8 g/L, 6 g/L, or about 4 g/L. The minimum amount of alginate produced by the strains of the present invention is about 2 g/L. In some embodiments, the amount of alginate produced by the strains of the present invention is about 2 to 100 g/L, 1 to 80 g/L, 2 to 60 g/L, 2 to 40 g/L, 2 to 20 g/L or about 2 to 10 g/L. In some embodiments, the amount of alginate produced by the strains of the present invention is about 10 to 100 g/L, 10 to 80 g/L, 10 to 60 g/L, 10 to 40 g/L or about 10 to 20 g/L. In some embodiments of the invention, the amount of alginate produced by the strains of the present invention is about 2 to 20 g/L, 20 to 40 g/L, 40 to 60 g/L, 60 to 80 g/L or about 80 to 100 g/L.

Methods and Cultures for Producing Alginate in Bacteria

The present invention provides methods for producing alginate comprising culturing mucoid bacteria. According to the present invention, alginate can be produced by any mucoid bacteria. In one embodiment of the invention, alginate is produced by gram-negative bacteria, for example, by bacteria of the genus *Pseudomonas* or *Azotobacter*. According to the invention, alginate can be produced using *A. vinelandii*, *A. chroococcum*, *P. putida*, *P. mendocina*, *P. fluorescens*, *P. maltophilia*, *P. cepacia*, *P. mallei*, *P. pseudomallei*, *P. alcaligenes*, *P. stutzeri*, *P. putrefaciens*, *P. acidovorans*, *P.*

*diminuta* or *P. aeruginosa* strains. In one preferred embodiment of the invention, alginate is produced using *P. aeruginosa*.

In some embodiments, the invention provides for methods of producing alginate by culturing bacteria with at least one genetic alteration that results in increased alginate production. In some embodiments, the genetic alteration results in the increased activity of a positive regulator of alginate production compared to wild-type bacteria. For example, the present invention provides for methods of producing alginate by culturing bacteria that have increased AlgU, MucE, ClpP, ClpP2 and/or ClpX activity. In some embodiments of the present invention, positive regulators of alginate production can be overexpressed from an exogenous DNA source, e.g., from plasmid DNA. For example, plasmids containing sequences encoding for ClpP, ClpP2, and/or ClpX can be expressed to increase alginate production in bacteria. In other embodiments of the present invention, positive regulators of alginate can be overexpressed from an endogenous DNA source, due to the alteration of endogenous regulatory sequences. For example, mutations in regulatory sequences such as promoters or enhancers that result in overexpression of a positive regulator or underexpression of a negative regulator of alginate production are contemplated. Additionally, mutations in regulatory sequences on exogenous DNA sources are also contemplated.

In one embodiment of the present invention, the bacteria used to produce alginate have increased MucE activity compared to wild-type bacteria. The activity of MucE can be increased using any technique known in the art. For example, MucE may be overexpressed by providing an exogenous mucE gene, for example, on a plasmid. Alternatively, endogenous mucE may be overexpressed, for example, by increasing the strength of the mucE promoter or by increasing the stability of the MucE protein. Another aspect of the present invention is to provide methods for producing alginates in bacteria wherein the bacteria overexpress a protease that negatively regulates MucA, for example, ClpP, ClpP2 and/or ClpX.

In another embodiment of the present invention, the bacteria used to produce alginate have increased activity of one or more positive regulators of alginate production. For example, bacteria of the present invention may have increased MucE and ClpP activity, MucE and ClpP2 activity, or MucE and ClpX activity.

In another embodiment of the present invention, the bacteria used to produce alginate express a positive regulator of alginate production under the control of an inducible system. For example, the bacteria of the present invention may contain mucE, clpP, clpP2 and/or clpX under the control of an inducible promoter, e.g. an arabinose-inducible promoter or an IPTG-inducible promoter, such that levels of MucE, ClpP, ClpP2 and/or ClpX and therefore alginate production, increase in the presence of arabinose (e.g., about 0.5-1% of arabinose) or IPTG. Other inducible systems which are known to those of skill in the art can also be used according to the present invention.

In some embodiments, the invention provides for the production of alginate by culturing bacteria that express an overactive protein that is a positive regulator of alginate production. An overactive protein has greater activity than the corresponding wild-type protein in the same condition. The activity can be, for example, increased protease activity or increased kinase activity. For example, the present invention contemplates not only bacteria that express increased levels of MucE, ClpP, ClpP2 and/or ClpX proteins, but also bacteria that express mutants of MucE, ClpP, ClpP2 and/or ClpX that show increased activity. The invention includes, for example, bacteria that express ClpP, ClpP2 and/or ClpX proteins that show increased protease activity as compared to wild-type ClpP, ClpP2 and/or ClpX proteins.

In some embodiments, the bacteria used to produce alginate have about a 1.5 fold, a 2 fold, a 3 fold, a 4 fold, 5 fold or about a 10 fold increase in MucE, ClpP, ClpP2 and/or ClpX activity compared to wild-type bacteria. In some embodiments, the bacteria used to produce alginate express MucE, ClpP, ClpP2 and/or ClpX protein at about 1.5 fold, 2, fold, 3 fold, 4 fold, 5 fold or about 10 fold higher level than wild-type bacteria. In some embodiments, the bacteria used to produce alginate express MucE, ClpP, ClpP2 and/or ClpX proteins that are about 1.5 fold, 2 fold, 3 fold, 4 fold, 5 fold or about 10 fold more stable than in wild-type bacteria. In some embodiments, the bacteria used to produce alginate express MucE, ClpP, ClpP2 and/or ClpX proteins and are about 1.5 fold, 2 fold, 3 fold, 4 fold, 5 fold or about 10 fold more stable than wild-type bacteria. In some embodiments, the bacteria used to produce alginate are about 1.5 fold, 2 fold, 3 fold, 4 fold, 5 fold or about 10 fold more stable than wild-type bacteria.

In another embodiment of the invention, the bacteria express lower levels or activity of factors that negatively regulate the production of alginate. For example, the present invention provides for methods of producing alginate by culturing bacteria that have decreased MucA, MucB, MucD and/or KinB activity. In some embodiments of the present invention, the activity of negative regulators of alginate production is reduced by decreased levels of production, by decreased levels of activity, and/or by decreased levels of stability. Alterations that result in decreased activity include mutations that result in alterations in protein coding sequences, e.g. mutations that result in premature termination codons and/or mutations that result in nonfunctional proteins and/or mutations that delete the gene completely. Alterations that result in decreased activity include mutations that affect regulator sequences and reduce transcription or translation of factors that negatively regulate the production of alginate. Alternations that result in decreased activity also include exposure to RNAi or other treatments that decrease levels of factors that negatively regulate the production of alginate.

In another embodiment of the invention, the bacteria used to produce alginate will have decreased MucD activity and decreased AlgW activity as compared to wild-type bacteria. In some embodiments, the bacteria used to produce alginate have about a 1.5 fold, a 2 fold, a 3 fold, a 4 fold, a 5 fold or about a 10 fold decrease in MucD and/or AlgW activity as compared to wild-type bacteria. In some embodiments, the bacteria will have decreased MucD activity and a deletion in AlgW (no AlgW activity). In other embodiments, the bacteria will have a deletion in MucD (no MucD activity) and decreased AlgW activity. In a preferred embodiment of the invention, alginate can be produced using bacteria with a deletion of both MucD and AlgW.

In one embodiment of the invention, the bacteria used to produce alginate have a mutation in mucA that results in production of a truncated MucA protein. The truncation may be, for example, the result of an insertion, deletion or amino acid change that results in a premature termination codon. The truncation may, for example, be a C-terminal deletion. A C-terminal deletion may result, for example, in a MucA protein of between about 20 and 160 amino acids in length, 20 and 140 amino acids in length, 20 and 120 amino acids in length, 20 and 100 amino acids in length, 20 and 75 amino acids in length or between about 20 and 50 amino acids in length. A C-terminal deletion may also result in a MucA protein about 55, 56, 57, 58, 59, 60, 61, 62, 63, 64 or 65 amino acids in length. In one embodiment, the C-terminal deletion results in a MucA protein about 59 amino acids in length.

In one embodiment of the invention, the bacteria used to produce alginate express a MucA protein that lacks one or more domains of MucA. In one embodiment, the MucA protein lacks the transmembrane domain or a portion of the transmembrane domain. In another embodiment, the MucA protein lacks the transmembrane domain and the periplasmic domain. In one embodiment, the MucA protein includes about amino acids 1 to 20, 1 to 30, 1 to 40, 1 to 50, 1 to 60, 1 to 70, 1 to 80, 1 to 84 or about 1 to 90. In one embodiment of the invention, the MucA protein includes amino acids 1 to 59. In one embodiment of the invention, the MucA protein includes about amino acids 1 to 84 and amino acids 104 to 194. In one embodiment of the invention the MucA protein includes a mutation or mutations in the transmembrane domain that disrupt MucA protein localization.

In one embodiment of the invention, the MucA protein or a fragment thereof is fused to additional amino acids. The additional amino acids may be, for example, amino acids from a different protein, amino acids from a non-consecutive region of MucA or other amino acids sequences. In one embodiment, the additional amino acids are expressed as a result of a frameshift mutation. In one embodiment of the invention, a frameshift mutation results in a protein about 60, 70, 80, 90, 100, 125, 150 or about 175 amino acids in length. In one embodiment of the invention, a frameshift mutation results in a protein about 90, 91, 92, 93, 94, 95, 96, 97, 98, 99 or about 100 amino acids in length. In one embodiment, the frameshift mutation results in a protein about 94 amino acids in length.

In another embodiment of the invention, the bacteria used for alginate production have a transposon located upstream of the mucA gene. In some embodiments of the invention, the bacteria used for alginate production have a transposon located in a mucA regulatory region that results in decreased production of MucA protein as compared to wild-type. In some embodiments of the invention, the transposon insertion results in a null allele of mucA.

In another embodiment of the present invention, the bacteria used to produce alginate have decreased activity of at least two negative regulators of alginate production. For example, bacteria of the present invention may have decreased MucA and MucB activity, decreased MucA and MucD activity, decreased MucB and MucD activity, or decreased MucA, MucB and MucD activity.

In some embodiments, the bacteria used to produce alginate have about a 1.5 fold, a 2 fold, a 3 fold, a 4 fold, 5 fold or about a 10 fold decrease in MucA, MucB, MucD and/or KinB activity compared to wild-type bacteria. In some embodiments, the bacteria used to produce alginate express MucA, MucB, MucD and/or KinB protein at about 1.5 fold, 2 fold, 3 fold, 4 fold, 5 fold or about 10 fold lower level than wild-type bacteria. In some embodiments, the bacteria used to produce alginate express MucA, MucB, MucD and/or KinB proteins that are about 1.5 fold, 2 fold, 3 fold, 4 fold, 5 fold or about 10 fold less stable than in wild-type bacteria.

In some embodiments of the invention, the bacteria used to produce alginate have increased activity of at least one positive regulator of alginate production and decreased activity of at least one negative regulator of alginate production. In one embodiment of the invention, alginate can be produced using bacteria with decreased MucA activity and increased MucE, ClpP, ClpP2 and/or ClpX activity.

The present invention also provides methods for producing alginates in bacteria that lack one or more endogenous endotoxin biosynthesis genes. Endotoxin genes are any genes that are expressed by bacteria that cause toxicity to eukaryotic cells, including, but not limited to, toxicity mediated by the endotoxin lipopolysaccharide (LPS). Other toxin genes carried on the so-called "pathogenicity island" or "type III secretion system" are generally repressed in *P. aeruginosa* during the overproduction of alginate (Wu, W., et al., *J Bacteriol* 186:7575-85 (2004)). However, in some embodiments of the invention, these genes can be removed, for example, through homologous recombination using a mutant allele cloned into the *Pseudomonas* suicide vector (pEX100T).

The present invention also provides methods for producing alginates in bacteria that are stable. By the term "stable bacteria" is meant a bacterial strain that does not revert to a non-mucoid phenotype within about 14 days. In addition, bacterial strains that do not convert to a non-mucoid phenotype within about 15, 16, 17, 18, 19, 20, 21, 22, 23, 24, 25, 26, 27, 28, 29, 30, 40, 50, 60, 70, 80, 90, 100, 110, 120, 130, 140, 150, 160, 170 or within about 180 days are also contemplated. In addition, bacterial strains that do not revert to the non-mucoid phenotype within about 14 to 60 days, 14 to 50 days, 14 to 40 days, 14 to 30 days, 14 to 20 days, 2-3 months, 2-4 months, 2-5 months, 2-6 months, 3-4 months, 3-5 months and 3-6 months are also contemplated.

In some embodiments of the present invention, the alginate-producing bacteria are grown under certain conditions. The bacteria may be grown on agarose plates and/or in liquid culture, for example in LB broth. When *Pseudomonas* is used as the alginate-producing bacteria, *Pseudomonas* Isolation Agar (PIA) can be used, which includes Irgasan™. Irgasan™ is a potent broad spectrum antibiotic that is not active against *Pseudomonas*. PIA is also useful in isolating *Pseudomonas aeruginosa* from other pseudomonads based on color because PIA contains magnesium chloride and potassium sulfate to enhance the formation of the blue or blue-green pyocyanin pigment by *Pseudomonas aeruginosa*.

The bacteria of the invention may be grown at a certain temperature. For example, the bacteria may be grown at a temperature of about 42, 37 or 30° C. In a preferred embodiment, the bacteria are grown at 37° C.

The bacteria of the invention can be grown on a solid agar surface with a concentration of about 0.8% agarose and higher, or in liquid broth. Bacteria can also be grown in a regular shake flask in a temperature-controlled incubator or in a continuous bioreactor system with temperature, nutrient, dissolved oxygen and/or pH control.

In some embodiments of the present invention, the alginate is produced by mass production. Mass production includes growing and isolating large quantities of alginate, for example, by growing bacteria, for example *Pseudomonas aeruginosa*, in a bioreactor and purifying alginate from the supernatant. In some embodiments, mass production requires that the bacterial strains are stable producers of alginate for about 14 to 120 days.

Alginate Testing, Isolation and Purification

One skilled in the art will appreciate the various known direct and/or indirect techniques for detecting the presence of alginate, any of which may be used herein. These techniques include, but are not limited to, antibody-based detection methods and optical density-based measurements. For example, alginate-specific antibodies can be used to observe the alginate-induced specific fluorescence using an immunofluorescence technique as described, for example by Bragonzi, A. et al., *J. Infec. Dis.* 192:410-9 (2005). In addition, high-performance liquid chromatography (HPLC) can be used to measure the components of mannuronate and guluronate after a sample is completely hydrolyzed, for example by treatment with a strong acid such as sulfuric acid ($H_2SO_4$). Phenotypic based assays, for example, identification of mucoid phenotypes, are also contemplated in the present invention.

According to the present invention, alginate can be isolated and purified using any method known in the art. For example, alginate can be purified from bacterial cultures by centrifuging the culture to remove bacterial cells, and then treating the alginate-containing supernatant with ethanol or propan-2-ol.

Furthermore, in another embodiment of the invention, $CaCl_2$ can be used to remove endotoxic contaminants, such as LPS. In certain embodiments of the invention, alginate can be precipitated from raw bacterial alginate samples (i.e., the supernatant collected after centrifugation to remove bacterial cells). In some embodiments, the supernatant sample from which alginate is purified contains about 0.01 mg/ml, 0.05 mg/ml, 0.10 mg/ml, 0.20 mg/ml, 0.50 mg/ml, 1.00 mg/ml or about 5.00 mg/ml of alginate. In some embodiments of the invention, the supernatant sample from which alginate is purified contains about 0.01 to 0.10 mg/ml, 0.01 to 0.20 mg/ml, 0.01 to 0.50 mg/ml, 0.01 to 1.00 mg/ml or about 0.01 to 5.00 mg/ml of alginate. In some embodiments of the invention, the supernatant sample from which alginate is purified contains about 0.05 to 0.10 mg/ml, 0.05 to 0.20 mg/ml, 0.05 to 0.50 mg/ml, 0.05 to 1.00 mg/ml or about 0.05 to 5.00 mg/ml. In one embodiment of the invention, the alginate concentration is about 0.1 mg/ml.

In other embodiments of the invention, alginate can be prepared from bacterial cultures in which alginate is present at a concentration of about 10 μg/ml protein, 20 μg/ml protein, 30 μg/ml protein, 40 μg/ml protein, 50 μg/ml protein, 60 μg/ml protein, 70 μg/ml protein, 80 μg/ml protein, 90 μg/ml protein, 100 μg/ml protein, 150 μg/ml protein, 200 μg/ml protein, 250 μg/ml protein, 300 μg/ml protein, 350 μg/ml protein, 400 μg/ml protein, 450 μg/ml protein, 500 μg/ml protein, 550 μg/ml protein, 600 μg/ml protein or about 1000 μg/ml protein. In some embodiments of the invention, the alginate is present at a concentration of about 10-1000 μg/ml protein, 50-500 μg/ml protein, 100-400 μg/ml protein or about 200-300 μg/ml protein. In some embodiments of the invention, the alginate is present at a concentration of about 10-500 μg/ml protein, 10-400 μg/ml protein, 10-300 μg/ml protein, 10-200 μg/ml protein, 10-100 μg/ml protein or about 10-50 μg/ml protein.

In other embodiments, the sample from which alginate is purified contains a certain concentration of endotoxin, such as LPS. For example, the concentration of endotoxin can be about 0.01 mg/ml, 0.05 mg/ml, 0.10 mg/ml, 0.20 mg/ml, 0.30 mg/ml, 0.40 mg/ml or about 0.50 mg/ml. In some embodiments, the endotoxin concentration is from about 0.01 mg/ml to 1.0 mg/ml, 0.05 mg/ml to 1 mg/ml, 0.25 mg/ml to 0.75 mg/ml or about 0.5 mg/ml to 1.0 mg/ml. In one embodiment of the invention, the endotoxin is LPS and the concentration is about 0.5 mg/ml. LPS concentrations can be determined using any known methods in the art, including, but not limited to, *Limulus* amoebocyte assay and thiobarbituric acid assay.

In other embodiments of the invention, the concentration of $CaCl_2$ used to precipitate the alginate is about 0.01 mg/ml, 0.05 mg/ml, 0.10 mg/ml, 0.25 mg/ml, 0.50 mg/ml, 1.0 mg/ml, 5.0 mg/ml, 10.0 mg/ml, 15 mg/ml or about 20 mg/ml. In other embodiments, the concentration of $CaCl_2$ used to precipitate alginate is about 0.01 to 50 mg/ml, 0.05 to 25 mg/ml, 0.05 to 20 mg/ml, 0.05 to 10 mg/ml, 0.05 to 5 mg/ml, 0.05 to 1 mg/ml, 0.05 to 0.50 mg/ml or about 0.05 to 0.25 mg/ml. In one embodiment, the concentration of $CaCl_2$ used is about 0.10 mg/ml.

In some embodiments, the alginate is free or substantially free of endotoxins. As used herein, the term "free of" means that there are no endotoxins present in the sample. As used herein, the term "substantially free" means that the concentration of endotoxin in the sample is below the minimum concentration that causes toxicity. In some embodiments, the alginate is isolated to a specific purity. For example, in some embodiments, the alginate is at least 50% pure, at least 60% pure, at least 70% pure, at least 80% pure, at least 90% pure, at least 95% pure, at least 97% pure, at least 98% pure, at least 99% pure or at least 99.5% pure. In other embodiments, the alginate isolated is about 50% pure, about 60% pure, about 70% pure, about 80% pure, about 90% pure, about 95% pure, about 97% pure, about 98% pure, about 99% pure or about 99.5% pure.

Alginate Compositions and Uses

The present invention provides for biological cultures comprising stable mucoid bacteria. According to the present invention, biological cultures are compositions comprising bacteria. The biological cultures can be liquid, for example in LB broth, or solid, for example in agarose. The biological cultures can be frozen cultures, cultures in stationary phases, and/or cultures in growth phases.

In some embodiments, the present invention also provides compositions comprising alginate. In some embodiments, the compositions comprise alginate produced by bacteria that have increased MucE activity as compared to wild-type bacteria. In other embodiments, the compositions comprise alginate produced by bacteria that have decreased MucA activity as compared to wild-type bacteria. In another embodiment, the compositions comprise alginate produced by bacteria that have a truncation mutation in mucA. In another embodiment, the compositions comprise alginate produced by bacteria that have a transposon insertion before the mucA gene. The present invention also provides for compositions that comprise alginate produced by bacteria that have increased protease activity, for example, increased ClpX, ClpP or ClpP2 activity. In another embodiment, the composition comprises alginate produced by bacteria that have decreased MucA activity as compared to wild-type bacteria and increased ClpX, ClpP and/or ClpP2 activity as compared to wild-type bacteria. In another embodiment, the composition comprises alginate produced by bacteria that have decreased MucA activity as compared to wild-type bacteria, increased MucE activity as compared to wild-type bacteria and increased ClpX, ClpP and/or ClpP2 activity as compared to wild-type bacteria. Furthermore, the invention provides compositions that comprise alginate produced by bacteria that are stable for about 14 to 90 days. In yet another embodiment, the invention provides for compositions comprising alginate produced by bacteria that lack one or more endogenous endotoxin genes.

The isolated bacterial alginate of the present invention can be used as, for example, gelling, thickening, stabilizing, swelling, and viscosity imparting agents. Thus, the isolated bacterial alginate of the present invention is useful in, for example, the food, textile, dental, pharmaceutical, cosmetic, and paper industries.

It can serve as a thickening agent in, for example, food items, such as ice cream, salad dressing, pet food chunks, low fat spreads, sauces and pie filings. Bacterial alginates can also be used in other diverse applications including for fixation and color in textile printing, for improving surface quality in paper and board treatments, for improving bendability of rods, for increasing aggregate size in flocculation processes in water treatment, for forming slits in can sealings, for concentrating latex during rubber extraction from plants, for reducing rates of surface drying in production of ceramics and foods, or for immobilization of cells.

The isolated bacterial alginate of the present invention can also be incorporated into wound dressings to provide a moist surface for healing. Alginate fibers trapped in a wound are readily biodegraded. Dressings with alginate are used to treat ulcers in diabetic patients. Propylene glycol alginate has been used as an acid-stable stabilizer for uses such as preserving the white fluffy head of foam on beers. Furthermore, the bacterial alginates of the present invention can be used to sequester cations, such as iron, from solutions, and therefore can be useful in filtering systems. Alginate absorbs radioactive elements, heavy metals and free radicals. Because alginate cannot be broken down by bile or saliva and cannot be absorbed by the body, it is secreted from the body together with the heavy metals and radioactive substances.

In order to further illustrate the present invention, specific examples are set forth below. It will be appreciated, however, that these examples are illustrative only and are not intended to limit the scope of the invention.

EXAMPLES

Materials and Methods

The following materials and methods apply generally to all the examples disclosed herein. Specific materials and methods are disclosed in each example, as necessary.

The practice of the present invention will employ, unless otherwise indicated, conventional techniques of cell biology, cell culture, molecular biology (including PCR), vaccinology, microbiology, recombinant DNA, and immunology, which are within the skill of the art. Such techniques are explained fully in the literature. See, for example, *Molecular Cloning A Laboratory Manual,* 2d Ed., Sambrook et al., ed., Cold Spring Harbor Laboratory Press (1989); *DNA Cloning, Volumes I and II,* D. N. Glover ed., (1985); *Oligonucleotide Synthesis,* M. J. Gait ed., (1984); Mullis et al. U.S. Pat. No. 4,683,195; *Nucleic Acid Hybridization,* B. D. Hames & S. J. Higgins eds. (1984); *Transcription And Translation,* B. D. Hames & S. J. Higgins, eds. (1984); Freshney, R. I., *Culture Of Animal Cells,* Alan R. Liss, Inc. (1987); *Immobilized Cells And Enzymes,* IRL Press (1986); Perbal, B., *A Practical Guide To Molecular Cloning* (1984); the treatise, *Methods In Enzymology,* Academic Press, Inc., N.Y.; *Gene Transfer Vectors For Mammalian Cells,* J. H. Miller and M. P. Calos eds., Cold Spring Harbor Laboratory (1987); *Methods In Enzymology, Vols.* 154 and 155, Wu et al. eds.; *Immunochemical Methods In Cell And Molecular Biology,* Mayer and Walker, eds., Academic Press, London, (1987); and in Ausubel et al., *Current Protocols in Molecular Biology,* John Wiley and Sons, Baltimore, Md. (1989). Each of the references cited in this paragraph is incorporated herein by reference in its entirety.

Strains and Plasmids

*E. coli* DH5α was used as the host for molecular cloning. The *E. coli* strains were grown in Lennox broth (LB), or LB agar supplemented with carbenicillin (100 µg/ml), gentamicin (13 µg/ml), tetracycline (15 µg/ml) or kanamycin (40 µg/ml), when required. *P. aeruginosa* strains were grown at 37° C. (unless specified) in LB broth, LB agar and *Pseudomonas* Isolation Agar (PIA, Difco) plates (supplemented with 300 µg/ml of gentamycin or carbenicillin, when required). The parental strains of *P. aeruginosa* for conjugation were grown at 42° C. in LB broth.

Transformation, Conjugation, Transposon Mutagenesis and Complementation Analysis Either electroporation or a chemical transformation method was used for the transformation of *E. coli*. A standard *Pseudomonas* conjugation protocol was followed with the following modifications. *E. coli* SM10 λpir carrying pFAC and *P. aeruginosa* strains were grown in 2 ml LB broth overnight at 37° C. and 42° C., respectively. The cell density of the cultures was measured by optical density at 600 nm and adjusted to a ratio of 1:1, which was equivalent to $8 \times 10^8$ cells for matings. The mixed cultures were incubated on LB plates for 6 h at 37° C. The cells were harvested and washed in LB broth. The final cell mixtures in a volume of 1 ml were spread on 8 PIA plates (50 ml each) supplemented with gentamicin. The conjugal pairs were incubated at 37° C. for 24 h for selection and screening exconjugants with a mucoid colony morphology. Such mutants were isolated and purified a minimum of 3 times. Mutants were frozen in 10% skim milk in a −80° C. freezer.

Biparental conjugations were carried out for transposon mutagenesis, using the pFAC carrying *E. coli* SM10 λpir as the donor strain and PAO581 as recipient strain. After 4-6 hrs of mating of *P. aeruginosa* and *E. coli* cells on LB plates at 37° C., bacteria were streaked onto PIA plates supplemented with 300 µg/ml of gentamycin. Non-mucoid colonies were subjected to further genetic analyses. The chromosomal DNA of non-mucoid mutants was prepared by using the QIAamp genomic DNA kit. About two micrograms of DNA was digested by SalI overnight at 37° C., followed by purification and self-ligation using Fast-Link DNA ligase (Epicentre). The circular closed DNA was used for inverse PCR using GM30UT and GM50UT primers designed based on the gentamycin resistance gene and the PCR products were purified and sequenced. Triparental conjugations, using pRK2013 as the helper plasmid, were conducted for genetic manipulations of *P. aeruginosa* PAO581 and PAO1 strains.

Pulsed-Field Gel Electrophoresis (PFGE) and Southern Hybridization

PFGE coupled with southern hybridization analyses were applied for the genome organization comparison between *P. aeruginosa* PAO581 and PAO1 as previously described. Southern blot hybridization was also applied to monitor the copy number of transposon insertion using the gentamycin resistance gene ($Gm^r$) as the probe template.

Western Blot Analyses

Western blots were performed according to the following protocol. The bacterial cells were harvested from LB broth (supplemented with 150 µg/ml of carbenicillin and 5 mM of IPTG). The cell density at 600 nm ($OD_{600}$) was measured and equal amounts of bacterial cells for each sample were pelleted. The bacterial cells were washed with cold PBS buffer (pH 7.4) once and then pelleted for protein extraction. The total cellular protein extracts were prepared using ReadyPreps™ kit (Epicentre). Protein samples were heated at 95° C. for 5 min, electrophoresed on an SDS-PAGE gel (15% acrylamide), and transferred onto a nitrocellulose membrane (pore size 0.1 µm, Schleicher & Schuell). Immunoblots were developed by using rat anti-HA monoclonal antibody (Roche) or rabbit anti-RNAP (RNA polymerase α-subunit) polyclonal antibody (Courtesy by M. J. Chamberlin, UC-Berkely) as the primary antibody, and Horseradish peroxidase-labeled goat anti-rat (Roche) or anti-Rabbit IgG (Kirkegaard & Perry laboratories) as the secondary antibody. Enhanced chemiluminescence ECL (Amersham Biosciences) was used for detection.

β-galactosidase Activity Assay

Assays were based on the method as originally described by Miller (In *Experiments in Molecular Genetics,* J. H. Miller, ed., Cold Spring Harbor Laboratory, Cold Spring Harbor, N.Y. (1972), pp. 352-355) with the following modification. The cells of NH1-3 were grown on PIA plates in triplicate for 24 h at 37° C. The cells were harvested in PBS and cell density was measured by $OD_{600}$. Samples were assayed after SDS/chloroform permeabilization of the cells.

The *P. aeruginosa* strains carrying the $P1_{algU}$ promoter-lacZ fusion were grown on PIA plates in triplicate at 37° C., and were harvested and resuspended in cold PBS buffer. The optical density at 600 nm was recorded and the β-galactosidase activity was measured after SDS/chloroform permeabilization for each sample. The Miller unit is equivalent to $1000*(A_{420}/-1.75*A_{550}/OD_{600}/ml/min)$, where $A_{420}$ and $A_{550}$ is the absorbance at 420 nm and 550 nm, respectively. The experiments were carried out in triplicate at least three times.

Nucleotide Sequence Accession Number

The annotated nucleotide sequence of algUmucABCD in PAO581 was submitted to the NCBI and assigned the GenBank accession number, EF635219.

DNA Manipulations

Two steps of polymerase chain reaction (PCR)-based cloning were used for general cloning purposes. First, the target genes were amplified by high-fidelity PCR using the appropriate primer sets containing the built-in restriction sites followed by cloning into pCR4-TOPO. The DNA fragments were digested by restriction enzymes, gel-purified, and transferred to the shuttle vector pUCP20. All recombinant plasmids were sequenced to verify the absence of mutations with M13 universal forward and reverse primers using an ABI 3130 Genetic Analyzer at the Marshall University School of Medicine Genomics Core Facility. PCR reactions were performed with MasterAmp™ Taq DNA Polymerase (Epicentre) in 50 μl EasyStart PCR tubes (Molecular BioProducts) as previously described (Head, N. E., and H. Yu, *Infect. Immun.* 72:133-44 (2004)).

Inverse PCR (iPCR)

The mariner transposon and its junction region in pFAC were sequenced. A multiple cloning site (MCS) was identified immediately outside the 3' end of the gentamicin cassette within the transposon. To map the insertion site, an iPCR protocol was developed to utilize this convenient MCS. *Pseudomonas* genomic DNA was purified using a QIAamp genomic DNA kit. The DNA concentration was measured using the NanoDrop® ND-1000 spectrophotometer (NanoDrop Technologies). Two μg DNA was digested by restriction enzymes SalI or PstI at 37° C. overnight followed by gel purification. The fragmented DNA was ligated to form the circularly closed DNA using the Fast-Link™ DNA ligation kit (Epicentre). A volume of 1 μl ligated DNA was used as template for PCR using GM50UT and GM30UT according to the condition as follows, 94° C. for 1 min, 34 cycles consisting of 94° C. for 1 min, 58° C. for 2 min, and 72° C. for 2 min, and a final extension step consisting of 72° C. for 8 min. After PCR, the products were analyzed on a 1% agarose gel. The PCR products were purified using the QIAquick PCR purification kits and sequenced using GM50UT as described above.

Alginate and Protein Assays

The alginate assay was based on a previously published method (Knutson, C. A., and A. Jeanes, *Anal. Biochem.* 24:470-481 (1968)) with the following modifications. *P. aeruginosa* and mutants were grown on 50 ml PIA plates in triplicate for a period of 72 h. At various time points, bacterial growth was removed from plates and re-suspended in 40 ml phosphate-buffered saline (PBS; pH 7.4). The optical density at 600 nm ($OD_{600}$) was recorded. The alginate standard curve was made using D-mannuronic acid lactone (Sigma) in the range of 0-100 μg/ml. To measure the protein concentration, the cells in PBS were lysed in 1:1 ratio with 1M NaOH for 15 min. The protein assay was performed using the Bio-Rad $D_c$ Protein Assay kit. The range for protein standard (bovine serum albumin) curve was from 0.2 to 1.2 mg/ml.

RNA Isolation and RT-PCR

*P. aeruginosa* strains PAO1, VE2 and VE3 were grown on 50 ml PIA plates for 24 h at 37° C. The cells were harvested in 40 ml PBS and re-suspended based on $OD_{600}$ to produce a cell population of $10^9$ to $10^{10}$. Total RNA was isolated using a RiboPure™-Bacteria Kit (Ambion) followed by DNase treatment as supplied. The quality of RNA was evaluated on an Agilent 2100 bioanalyzer. RT-PCR was performed using a One-Step RT-PCR kit (Qiagen). One μg bacterial RNA was reverse-transcribed into cDNA at 50° C. for 30 min followed by PCR amplification: 94° C. for 15 min, 34 cycles consisting of 94° C. for 1 min, 58° C. for 2 min, and 72° C. for 2 min. The PCR products were analyzed on 1% agarose gel, and the intensity of bands was analyzed on a Typhoon 8600 Variable Mode Imager (Molecular Dynamics) with the ImageQuant (v. 5.2) Software.

Monoclonal Antibodies

The AlgU and MucB monoclonal antibodies used in the Examples are from previously published sources (Boucher et al., *J. Bacteriol.* 178:511-523 (1996); Schurr et al., *J. Bacteriol.* 178:4997-5004 (1996)) with a low level of cross-reactivity. The specificities of these antibodies are appropriate because the algU and mucB negative strains failed to display the respective AlgU and MucB proteins. Furthermore, two non-specific proteins of 50 kDa and 75 kDa from MucB and AlgU blots respectively were used as convenient internal controls to normalize the protein levels.

Southern Hybridization

A 754 by PCR product was amplified from acc1 of pUCP30T using GM-F and GM-R primers, which was purified via gel extraction and labeled with digoxygenin as described by the manufacturer (Roche Molecular Biochemicals). Agarose gels were soaked in 0.25 N HCl for 30 min, rinsed in $H_2O$, soaked in 1.5 M NaCl/0.5 M NaOH for 30 min and 1.5 M NaCl/0.5 M Tris-Cl, pH 8.0 for 30 min. A blotting apparatus (BIO-RAD Vacuum Blotter) was used with a filter paper wick, a Hybond-N+ membrane (Amersham Pharmacia Biotech), and transferred with 10×SSC transfer buffer for 2 h. After transfer, the membrane was rinsed in transfer buffer and UV cross-linked. Hybridization was done using the DIG High Prime DNA Labeling and Detection Starter Kit II (Roche Applied Science) and labeled probe described above.

Statistical Analysis

Analysis of alginate production β-galactosidase activity was done with one-way analysis of variance (ANOVA) followed by pairwise multiple comparisons with Holm-Sidak method. Analysis of normalized protein intensity was carried out with the means of each group in comparison with that of PAO1 using t test assuming unequal variance or ANOVA if multiple groups were compared. All analyses were performed with SigmaStat (v. 3.1, Systat Software) and SigmaPlot (v. 9.0, Systat Software) software.

Example 1

Mariner-Based Transposon Mutagenesis Approach to Identify Mucoid Mutants in *P. aeruginosa*

To investigate alginate regulation in *P. aeruginosa*, the versatile Tc1/mariner himar1 transposon carried on pFAC (GenBank Accession number DQ366300), a *Pseudomonas* suicide plasmid, was used to mutagenize the non-mucoid strains of *P. aeruginosa* coupled with a genetic screen for mucoid mutants. (The screen and results which are summarized in this example are described in detail in International PCT Published Application WO 2007/123721, published Nov. 1, 2007, which is herein incorporated by reference in its entirety.) The mutant phenotype for selection was mucoid, alginate-overproducing colony morphology. Colonies were grown on the *Pseudomonas* Isolation Agar (PIA), which includes Irgasan™, a potent broad spectrum antimicrobial that is not active against *Pseudomonas* (Irgasan™ is a trademark of Ciba-Geigy).

Figure 1:
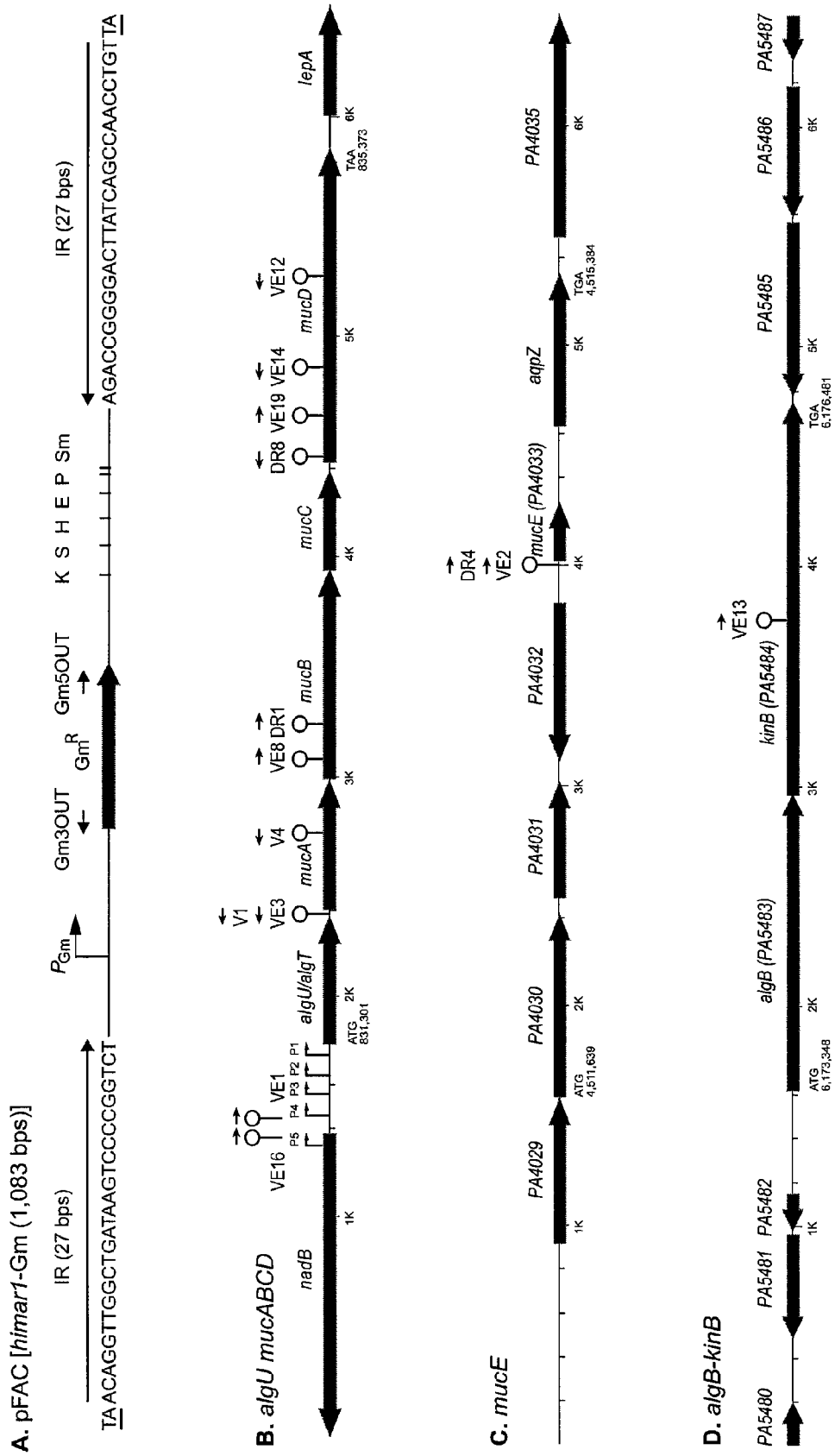

The sequence of the Tc1/mariner himar1 transposon was analyzed, and the nucleotide sequence of the transposon in pFAC has been deposited in GenBank with the accession no. DQ366300 (1473 bp, Tc1/himar1 mariner transposon vector pFAC). The schematic diagram of the mariner transposon region within pFAC is shown in FIG. 1A. The fact that mariner transposon was flanked by a region containing six unique restriction enzyme sites allowed for the development of an efficient inverse PCR procedure that was used to rapidly map transposon insertions in the genome.

Figure 2:
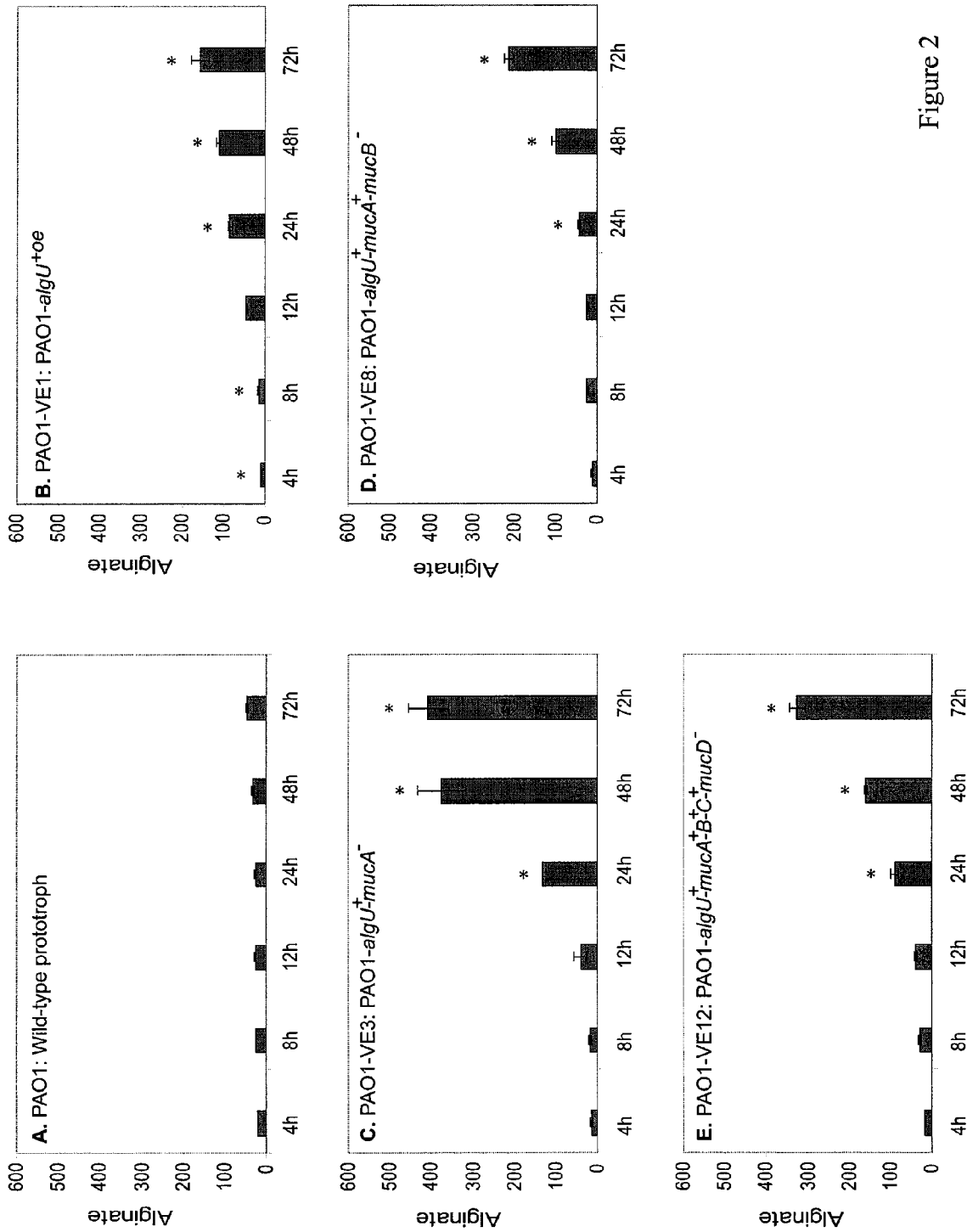
Figure 3:
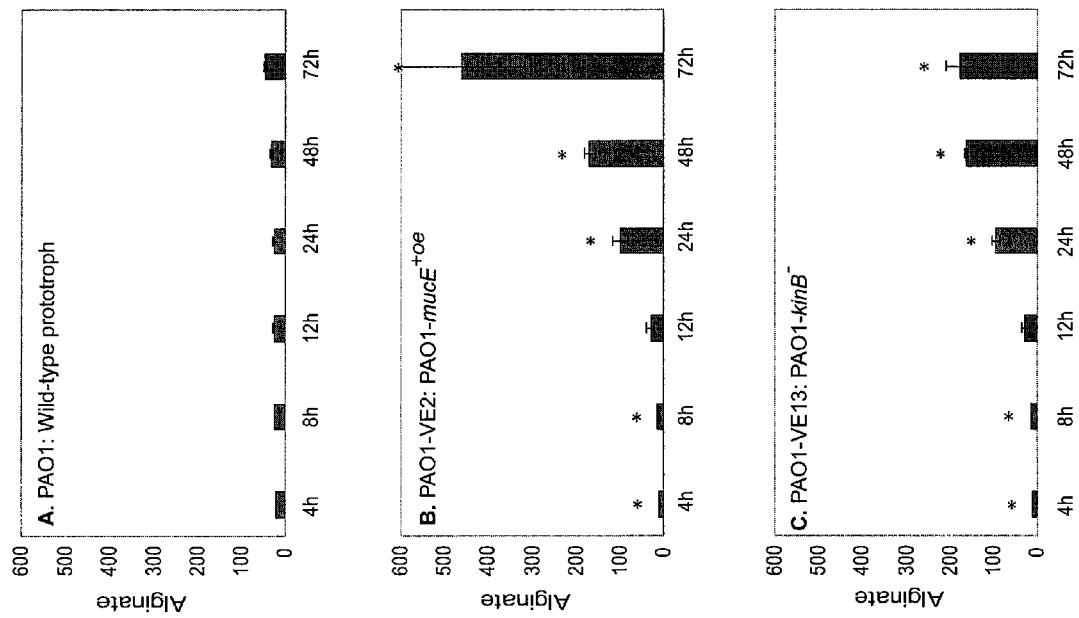
FIG. 3 shows alginate production in a mucE and kinB strain in comparison with the wild-type PAO1. The +oe superscript used in panel B refers to the overexpression of the mucE.

Many of the transposon insertions that were identified in the screen fell into three genomic regions, algU-mucABCD (FIG. 1B), mucE (FIG. 1C) and algB-kinB (FIG. 1D). Mucoid mutants identified in the screen were tested for alginate production (FIGS. 2 and 3). The highest producer of alginate is PAO1-VE3 (FIG. 2C). In this strain, the transposon inserted in a TA dinucleotide in front of mucA, but in an opposite direction of mucA transcription (FIG. 1B). This configuration of transposon insertion caused a loss of mucA transcription because the $P_{Gm}$ promoter is stronger than the promoters of algU mucABC operon since VE1 insertion is mucoid (FIG. 2B) and caused an elevation of AlgU expression. The PAO1-VE3 strain produces large amounts of alginate over a period of 72 hr such that plates are dripping due to alginate production. However, PAO1-VE3 reverts to the non-mucoid phenotype within about 3-4 days.

Transposon insertions in the promoter region of mucE (VE2) and in the coding region of kinB (VE13) also resulted in mucoid phenotypes. As shown in FIG. 3, alginate production was increased in these strains as well.

Another producer of large amounts of alginate contains a transposon in the algU mucABCD region. This is PAO1-VE12 (mucD mutant). Compared to PAO1-VE3, PAO1-VE12 is a more stable producer of alginate. The transposon mutants in FIG. 1B-1D carrying mutations in the mucD gene (DRB, VE19, VE14, and VE12) are more stable producers of alginate than the mucA mutants (V4, V1 and VE3), mucE (VE2) and kinB mutants (VE13). The non-mucoid revertants with the suppressor mutations can be readily isolated in VE3 and VE2 after 3-4 days at 37° C. whereas no non-mucoid mucD mutants have been isolated yet. The non-mucoid VE3 mutants carry mutations that inactivate or attenuate the activity of algU with the nucleotide sequences of VE3-NM1-4 as described in International PCT Published Application WO 2007/123721.

Example 2

Identification of the muc-25 Mutation as a Single Base Deletion ΔT180 in mucA

Another mucoid variant, PAO581, was also analyzed. PAO581 is a stable mucoid strain and does not easily revert to a non-mucoid phenotype. PAO581 was isolated in vitro following the incubation of the non-mucoid *P. aeruginosa* PAO with phage E79 (Fyfe, J. A. M. & Govan, J. R. W., *Journal of General Microbiology* 119, 443-450 (1980)). Since this strain carried undefined muc mutation(s) (designated as the muc-25 variant) (Fyfe, J. A. M. & Govan, J. R. W., Progress in industrial microbiology, pp. 45-83 (M. E. Bushell ed., Elsevier 1983)), it was first determined whether there were large genomic alterations in this strain. Using macrorestriction digestions of the genome coupled with separation by pulse field gel electrophoresis, no large-scale recombination, inversion, deletion, or amplifications were noted in PAO581 as compared to PAO1. This is consistent with earlier data (Fyfe, J. A. M. & Govan, J. R. W., Progress in industrial microbiology, pp. 45-83 (M. E. Bushell ed., Elsevier 1983)) which indicated that the mucoid phenotypes associated with muc mutation(s) designated muc-22, muc-23, and muc-25 are not associated with major changes in the DNA organization.

Previously, the muc-25 locus of PAO581 was roughly mapped to the region between pruAB (67.5 min) and hisI (69 min), very close to the algUmucABCD cluster (68 min) (Fyfe, J. A. M. & Govan, J. R. W., Progress in industrial microbiology, pp. 45-83 (M. E. Bushell ed., Elsevier 1983)). Therefore, the algUmucABCD genes of PAO581 were sequenced. A single base deletion at T180 of mucA was identified, leading to creation of a premature stop codon (TGA) at 285. The resulting frameshift encoded a truncated protein of 94 amino acids, which includes the N-terminal 59 amino acids of wild-type MucA and 35 divergent amino acids due to the frameshift (FIG. 9). This protein was probably located in the cytoplasm due to the absence of the transmembrane ($MucA_{84-104}$) and periplasmic ($MucA_{113-170}$) domains.

No mutation was found in the algU, mucB, mucC, and mucD genes of PAO581. To determine if this mutation could be identified in naturally-occurring mucoid *P. aeruginosa* isolates, the algU-mucA genes were sequenced in a series of variant mucoid isolates obtained from the lungs of transgenic CF mice which emerged after 6-12 months of chronic lung infection (Coleman, F. T., et al., *Proc Natl Acad Sci USA* 100:1949-1954 (2003)). Interestingly, the same mucA mutation as that of PAO581 was identified in one of the mucoid isolates. The wild-type (wt) mucA gene in PAO1 was replaced with the mucAΔT180 allele from PAO581 and the resultant strain, PAO1DR1, became mucoid, as expected. The mucoid phenotype of both PAO581 and PAO1DR1 could be suppressed by the introduction of wt mucA in trans on a plasmid (pUCP20T-mucA) (lac promoter). Thus, the previously uncharacterized muc-25 mutation was due to deletion of a single base of T180 in the mucA gene and has been designated the mucA25 allele.

Example 3

Transposon Insertions in tig, clpP, clpX, and clpP2 Render the muc-25 Mucoid PAO581 Non-Mucoid To determine if other factors might be important for the expression of the mucoid phenotype in PAO581, we used an approach of mariner transposon mutagenesis, which gives rise to high-density insertion of a TA-flanked gentamicin resistance marker into the chromosome of target bacteria including *P. aeruginosa* (Qiu, D., et al., *Proc Natl Acad Sci USA* 104:8107-8112 (2007); Rubin, E. J., et al., *Proc Natl Acad Sci USA* 96:1645-1650 (1999); Wong, S. M. and Mekalanos, J. J., *Proc Natl Acad Sci USA* 97:10191-10196 (2000)). In total, 86 non-mucoid mutants were isolated out of about 100,000 $Gm^r$ mutants of PAO581 screened. Insertion sites were identified by inverse PCR and sequencing. The majority of the non-mucoid mutants harbored a single insertion as confirmed by Southern hybridization using the $Gm^r$ cassette as a probe. As expected, most insertions were mapped to the known positive regulatory genes including algU, algR (Deretic, V., et al., *J Bacteriol* 171, 1278-1283 (1989)), algB (Goldberg, J. B. & Dahnke, T., *Mol Microbiol* 6:59-66 (1992)), and amrZ (algZ) (Baynham, P. J. & Wozniak, D. J., *Mol Microbiol* 22:97-108 (1996); Tart, A. H., et al., *J Bacteriol* 187:7955-7962 (2005)). These results, while confirming the previous findings, also validated the reliability and efficiency of the mariner-based transposon mutagenesis. There were about 2 to 3 independent transposon insertions in the first 7 genes of the 18 kb alginate biosynthetic operon, algD (PA3540), alg8 (PA3541), alg44 (PA3542), algK (PA3543), algE (PA3544), algG (PA3545), and algX (PA3546), as well as the unlinked algC (PA5322) gene. However, there were no insertions found in the other 5 genes, algL (PA3547), algI (PA3548), algJ (PA3549), algF (PA3450) and algA (PA3551). These results were consistent with previous findings, since transposon inactivation of algL is only possible if the transcription of the entire algD operon was suppressed (Jain, S. & Ohman, D. E., *Infect Immun* 73:6429-6436 (2005)) and inactivation of algI, algJ, and algF would not lead to a complete loss of mucoidy as these genes encode proteins involved in alginate acetylation, but not biosynthesis (Franklin, M. J., et al., *J Bacteriol* 186:4759-4773 (2004)).

Figure 4:
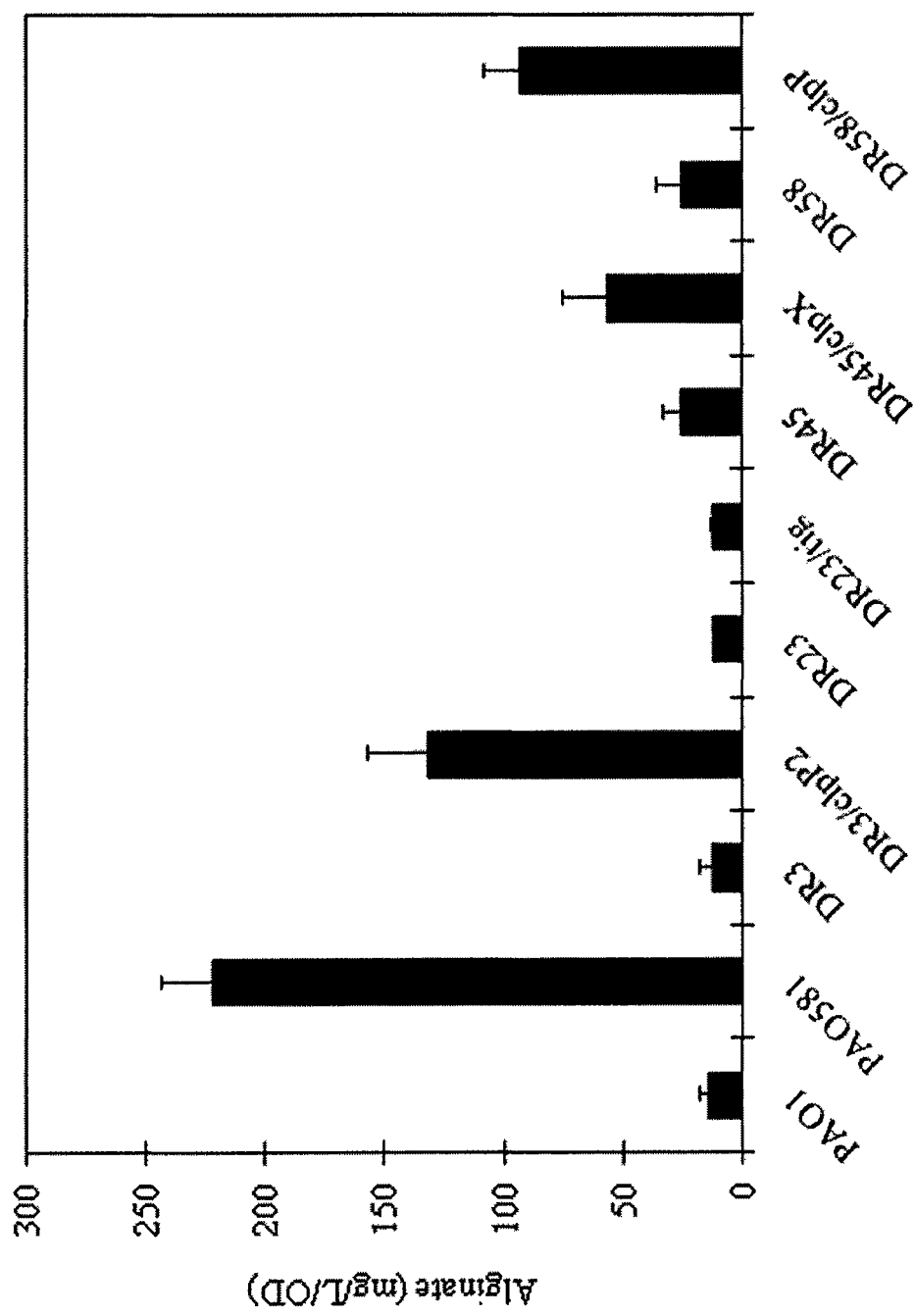
FIG. 4 shows alginate production in the P. aeruginosa wild-type and mutant strains. Genetic complementation tests were performed using pUCP20 vector (negative control) and with pUCP20 vector containing clpP2, tig, clpX or clpP sequences.

Other transposon insertions in the non-mucoid mutants mapped to the tig-clpP-clpX (PA1800-1802) polycistronic loci and a monocistronic locus of PA3326, a paralogous gene of clpP (designated clpP2). The clpP2 gene encodes a polypeptide of 201 amino acids, homologous to ClpP (encoded by PA1801, 213 amino acids). Eleven out of the fifty-one transposon insertions (21.6%) were mapped to the tig (2 insertions), clpP (3), clpX (4), and clpP2 (2) loci. Southern blot analyses confirmed that only a single copy of the transposon was inserted into the chromosome in these null mutants. The relevance of these genes to the mucoid conversion was confirmed by complementation tests. The mucoid phenotype and alginate synthesis could be restored to the tig (PAO581DR23), clpP (PAO581DR58), and clpX (PAO581DR45) null mutants by the pUCP20T borne tig-clpP-clpX (pUCP20T-tig-clpXP) in trans (FIGS. 4 and 8). In addition, introduction of pUCP20-clpP2 could restore mucoidy to the clpP2 null mutants of PAO581DR3 and PAO581DR9, suggesting that the ClpP2 protease is also required for the mucoid phenotype (FIGS. 4 and 8). However, the non-mucoid phenotype of the tig null mutants, PAO581DR23 and PAO581DR6, seemed to result from polar effects of the transposon insertion on the downstream clpP and clpX since pUCP20T-tig did not restore alginate synthesis (PAO581DR23) (FIGS. 4 and 8). Both pUCP20T-tig-clpXP and pUCP20T-clpXP induced a high level of alginate production in the tig mutant, PAO581DR23. To confirm the function of ClpXP and to verify that the transposon insertion did not cause other unknown mutations, we cloned the $Gm^R$ interrupted allele of PAO581DR58 (clpP::$Gm^R$) into the suicide vector pEX100T and used it to disrupt the clpP gene of PAO581. The resultant clpP mutant of PAO581 was non-mucoid, and the mucoid phenotype could be complemented by the plasmid borne clpP in trans.

Since the tig-clpP-clpX gene cluster was identified to be involved in the regulation of alginate synthesis, the tig-clpP-clpX cluster of PAO581 was subjected to sequence analyses. Compared with the tig-clpP-clpX cluster of the parental non-mucoid strain of PAO1, some missense mutations were found, suggesting that these polymorphisms could be required for the mucoid phenotype of PAO581. Therefore, the tig-clpXP and clpXP genes of PAO581 were cloned into pUCP20T to test for the mucoid induction in PAO1. However, over-expression of these PAO581-derived genes, tig-clpXP (PAO581), clpXP (PAO581) or the clpP2 gene from PAO581 (pUCP20T-clpP2), was not sufficient to cause the mucoid conversion in PAO1. Furthermore, plasmid-borne alleles from PAO581 were able to restore the mucoid phenotype of the non-mucoid mutants PAO581DR58 (clpP::$Gm^R$), PA581DR23 (tig::$Gm^R$), PAO581DR45 (clpX::$Gm^R$) and PAO581DR3 (clpP2::$Gm^R$). The pUCP20T-tig-clpXP genes from PAO1 could also complement in trans the null mutations of tig, clpX, and clpP in PAO581 (results were identical to what was seen with PAO581-derived alleles). These results indicate that the polymorphisms of the tig-clpXP loci were not responsible for the mucoid conversion in PAO581, and represented functional allelic variants that likely arose when PAO1 was mutagenized to produce the mucoid variant of PAO581 or during the laboratory passages of PAO581.

Example 4

AlgU Activity is Significantly Decreased in the clpP, clpX, and clpP2 Null Mutants AlgU activity was assayed in various strains, including PAO1, PAO581, and the isogenic null mutants of tig, clpX, clpP, and clpP2 as well as two other non-mucoid strains with mutations in algU (PAO581DR7) or algR (PAO581DR51). The P1 promoter of algU has been reported to be an AlgU-dependent autoregulatory promoter (Firoved, A. M. & Deretic, V., *J Bacteriol* 185:1071-1081 (2003); Schurr, M. J., et al., *J Bacteriol* 177:5670-5679 (1995)). The $P1_{algU}$ promoter-lacZ fusion was integrated into the CTX phage attachment site (attB) on the bacterial chromosome of PAO581 and the isogenic mutants (Hoang, T. T., et al., *Plasmid* 43:59-72 (2000)). AlgU expression was 2.2 fold higher in PAO581 than that in the wt non-mucoid strain PAO1 (P<0.001 ANOVA, P<0.05 Dunnett's test) thus validating that the mucoid phenotype of PAO581 was caused by the increased level of functional AlgU (FIG. 5). Furthermore, AlgU activity of the isogenic, non-mucoid tig, clpX, clpP, and clpP2 null mutants of PAO581 was comparable to that of PAO1, and was 2-3 fold lower than that of PAO581 (P<0.001 ANOVA, P<0.05 Dunnett's test for pair-wise comparisons).

Very low level of the β-galactosidase activity was detected in the algU null mutant PAO581DR7 (negative control), which was 2.8-fold and 6-fold lower than PAO1 and PAO581, respectively (data not shown). The AlgU activity was decreased slightly in the algR null mutant PAO581DR51 (positive control) but was 1.8-fold higher than that of PAO1 (data not shown). AlgR is an AlgU-dependent downstream regulatory gene for alginate synthesis (Deretic, V., et al., *J Bacteriol* 171:1278-1283 (1989)), and its disruption could not affect the activity of the upstream regulator AlgU. These results suggest that ClpX, ClpP and ClpP2 are involved in the increase in AlgU activity, which is associated with increased alginate synthesis and the subsequent development of the mucoid phenotype.

Example 5

Over-Expression of algU Restores the Mucoid Phenotype to the tig, clpP, clpX, and clpP2 Null Mutants of PAO581

The above results suggest that the tig and clp mutants could not degrade the anti-σ factor MucA protein to release AlgU, thus producing the non-mucoid phenotype in *P. aeruginosa*. If this is the case, over-expression of AlgU in these mutants should bypass the requirement for tig, clpP, clpX, and clpP2. Therefore, the pUCP20T-$P_{BAD}$-algU construct was introduced into these null mutants. All of these conjugants converted to the mucoid phenotype when inoculated onto PIA plates supplemented with 0.5-2.5% of arabinose, whereas in the absence of arabinose the strains remained non-mucoid on PIA plates. These results suggest that the endogenous AlgU is sequestered by the truncated MucA25 protein in the tig, clpX, clpP, and clpP2 null mutants of PAO581 as these cofactors are apparently needed for release of AlgU from the anti-sigma factor MucA.

Example 6

Both Truncated MucA Proteins and Intact tig-clpP-clpX and clpP2 are Required for the Mucoid Phenotype in *P. aeruginosa*

To determine if the conversion of *P. aeruginosa* to the mucoid phenotype is dependent on both a truncated MucA protein and the Clp proteases that could degrade the cytoplasmic portion of this sequestering anti-sigma factor, the HA tagged mucA25 and HA tagged wt mucA fusions were created in the pBAD/pUCP20T vector, and the constructs were transferred into PAO1, PAO581, PA581DR23 (tig::$Gm^R$), PAO581DR45 (clpX::$Gm^R$), PAO51DR58 (clpP::$Gm^R$), and PAO581DR3 (clpP2::$Gm^R$). As expected, there was no phenotypic change in wt PAO1 expressing HA-tagged muc25. However, over-expression of the mucA25 allele suppressed the mucoid phenotype in PAO581, while the vector control had no effects. Similarly, all of PAO581 strains carrying wt mucA allele in trans remained mucoid when arabinose was absent, but converted to non-mucoid when the level of arabinose was >0.01%. Similarly, the IPTG-inducible pVDtac24-based construct pDR206, carrying the HA tag-mucA fusion, and pDR207, carrying an HA tag-mucA22 fusion, could also suppress the mucoid phenotype of PAO581 under the IPTG induction. However, higher levels of inducers (>0.05% of arabinose or 5 mM of IPTG) were required for the mucA25 or mucA22 carrying constructs to suppress the mucoid phenotype of PAO581 as compared to the amount needed for the mucoid suppression by the wt mucA carrying constructs. These results indicate that the mucoid phenotype of PAO581 is due to the truncation of anti-σ factor MucA as a consequence of mucA25 mutation and that ClpXP might be responsible for degrading the N-terminus of MucA.

Example 7

Truncated N-Terminal MucA Proteins are Stabilized in the tig, clpX, clpP, and clpP2 Null Mutants The in vivo stability of MucA protein was monitored by Western blot analysis of the HA-tagged wt-MucA protein and HA-tagged MucA25 proteins in wt PAO1 and mucoid variant, PAO581. Similar levels of wt HA-MucA fusion protein (~25 kDa) could be detected in PAO1, PAO581 and the tig-clp mutants of PAO581 (data not shown), suggesting that the full-length HA-tagged MucA protein is stable in all of these genetic backgrounds. However, the levels of the truncated MucA25 (~15 kDa) proteins was 4.3-fold lower in PAO1 compared with PAO581 after the arabinose induction (FIG. 5). The levels of HA-tagged MucA25 proteins were also increased in the clp-mutants of PAO581 compared with PAO1 (FIG. 5). The level of HA-tagged MucA25 was >3-fold higher in PAO581DR3 (clpP2::$Gm^R$) and PAO581DR58 (clpP::$Gm^R$) than in PAO581 (FIG. 5). There was an accumulation of the MucA25 variant protein under the condition of arabinose induction in the null mutants of tig, clpX, clpP and clpP2 (FIG. 5). Therefore, in the absence of the ClpXP protease, MucA25 was not degraded, suggesting that this protease complex may be responsible for the degradation of the N-terminus of MucA25 to release the sequestered AlgU into the cytoplasm for activating the transcription of alginate biosynthetic genes. As shown in Table 1, mutations in clpP and clpX prevent a mucoid phenotype in a clinical strain CF24.

TABLE 1

Disruption of clpP and clpX in CF24

| Strain | Genotype | Phenotype | pUCP20T vector | pUCP20T-clpPX |
|---|---|---|---|---|
| CF24 | Clinical isolate | Mucoid | Mucoid | |
| CF24DR1 | CF24 clpP::$Gm^R$ | Non-mucoid | Non-mucoid | Mucoid |
| CF24DR2 | CF24 clpX::$Gm^R$ | Non-mucoid | Non-mucoid | Mucoid |

Example 8

Characterization of Alginate Produced from Bacteria

To compare alginate produced in bacteria to that produced in seaweed, alginate purified from *P. aeruginosa* and a commercially available seaweed alginate were analyzed. In these experiments, two bacterial strains were used, PAO1-VE19 (mucD mutant) and PAO578 (PAO1-mucA22) for the preparation of bacterial alginate. Bacteria were first grown at 37° C. on 50 ml PIA plates for 24-48 hours. Bacterial growth was removed from plates with PBS and suspended in a total volume of 50 ml PBS per plate. Bacterial suspensions were centrifuged to remove the cellular debris and pellets. The supernatants were precipitated with three volumes of cold ethanol, freeze-dried and resuspended in 10 ml PBS, and dialyzed in a large volume of cold PBS to remove the salts. VE19-1 alginate was dialyzed while VE19-2 was not-dialyzed. Seaweed alginate used was purchased from Sigma Aldrich as alginic acid (A-7003) extracted from *Macrocystis pyrifera* (Kelp).

The alginates were analyzed using the Viscotek Triple Detector System (Houston, Tex.), which makes use of four different technologies: Gel Permeation Chromatography (GPC), Flow Injection Polymer Analysis (FIPA), Dilute Solution Viscosity (DSV) and Dynamic Light Scattering (DLS). The analysis demonstrated that the physical properties of bacterial alginate are different from those of seaweed alginates. The data are summarized below in Table 2 and show, in particular, that the bacterial alginates are much more viscous than seaweed alginates.

TABLE 2

Physical analysis of three purified alginate samples produced by *P. aeruginosa* as compared to the seaweed alginates.

| Sample ID | MW (daltons) | Viscosity (dL/g) | Hydrodynamic radius (nm) | Reflection index | % Recovery | Calc. Conc. (mg/ml) |
|---|---|---|---|---|---|---|
| VE19-1 | 13,415,000 | 96.8 | 274 | 0.15 | 395 | 1.08 |
| VE19-2 | 14,815,000 | 97.3 | 283 | 0.15 | 365 | 0.82 |
| PAO578 | 18,605,000 | 97.6 | 306 | 0.15 | 399 | 0.44 |
| Seaweeds | 77,753 | 2.2 | 14 | 0.15 | 296 | 1.87 |

Example 9

Purification of Alginate with CaCl$_2$

When produced in bacteria, alginate samples can be contaminated with a major cell wall component of bacteria, lipopolysaccharide (LPS). LPS is a known endotoxin which can cause septic shock and inflammation. As a result, removal of LPS from alginate preparations to be used for example, in food or pharmaceutical compositions, is needed. Raw bacterial alginate samples (i.e., the supernatants that were collected after centrifugation to remove bacterial cells) were treated with calcium chloride. A concentration of 0.1 mg/ml CaCl$_2$ solution was sufficient to precipitate alginate at a concentration of 0.1 mg/ml. In contrast, P. aeruginosa lipopolysaccharide (L9143, Sigma-Adrich) at a concentration of 0.5 mg/ml could not be precipitated with a solution of 20 mg/ml CaCl$_2$. These results indicate that alginate can be precipitated from solution by CaCl$_2$ using conditions under which LPS does not precipitate. This allows for effective removal of LPS from bacterially produced alginates.

Example 10

P. aeruginosa MucE Caused Conversion to Mucoidy in P. fluorescens

Other Pseudomonas species have mucE homologs (FIG. 7). In order to determine if mucE of P. aeruginosa is functional in other Pseudomonas species, P. aeruginosa mucE was expressed in P. fluorescens. In these experiments, P. aeruginosa mucE was cloned into an arabinose-inducible vector, pHERD20T, which was created by replacing the P$_{LAC}$ promoter in pUCP20T with the P$_{BAD}$ promoter and araC gene from pBAD/Thio-TOPO (Invitrogen®). The arabinose-inducible mucE construct was transferred into P. fluorescens Pf-5 via conjugation. The P. fluorescens carrying the mucE construct remained non-mucoid on gentamicin (300 μg/ml) supplemented PIA plates and converted to a mucoid phenotype in the presence of 0.5-1% of arabinose. These results indicate that expression of P. aeruginosa MucE can cause conversion to mucoidy in other Pseudomonas strains.

Example 11

Genetic Construction of Alginate Producing Strain HD101

Strain HD101 will be constructed by a "clean" deletion of the mucD gene from P. aeruginosa PAO1ΔalgW (FIG. 10). We previously observed that inactivation of mucD with the pFAC transposon causes alginate overproduction. However alginate production by this strain is not stable and nonmucoid revertants can readily occur. We also noted that inactivation of the algW gene in the mucD mutant produced copious amounts of alginate with a low level of nonmucoid revertants. This strain displayed high sustained production of alginate (stable mucoid mutant).

AlgW and MucD control alginate production through overlapping and divergent pathways. When MucD is absent, alginate production occurs due to loss of quality control in the envelope. AlgW has a role in the degradation of an anti-sigma factor known as MucA. When MucA is degraded, the master regulator AlgU activates alginate production. Our data shows the algW/mucD double mutant has a lower rate of MucA degradation. This lower rate causes stable and controlled alginate production that is not detrimental to the organism.

To generate HD101, a vector will be constructed and named pEX100T-ΔmucD. Through several rounds of PCR amplification and subcloning a section of DNA will be generated with the upstream and downstream flanks near mucD but lacking the mucD coding sequence. The plasmid will be transferred to PAO1ΔalgW and selected for antibiotic resistance. Because the deletion vector lacks the Pseudomonas origin of replication, the DNA will be taken up by the organism and incorporated into the genome by homologous recombination. This strain will be resistant to the backbone antibiotic but will be sensitive to sucrose due to the presence of the sacB gene, which when expressed in the presence of sucrose kills the organism. The strain will be grown for several hours in nutrient rich media lacking antibiotics. DNA recombination will take place and mucoid strains will be selected that are sensitive to the antibiotic and resistant to sucrose. To confirm the mucD gene has been deleted, PCR amplicon sequencing and complementation analysis with mucD expressed from pHERD$_2$OT-mucD will be performed. Strain HD101 produces high amounts of alginate and remains stable. Furthermore, as this genetic manipulation will be performed by gene deletion without leaving antibiotic resistance markers behind, this strain can be further modulated to produce different types of alginate.

---

What is claimed is:

1. A biological culture comprising isolated stable mucoid *Pseudomonas aeruginosa* bacteria that produce alginate, wherein the bacteria are genetically modified *Pseudomonas aeruginosa* bacteria having increased protease activity of a ClpP, ClpP2, or ClpX polypeptide as compared to wild-type *Pseudomonas aeruginosa* bacteria that is the result of transformation of the *Pseudomonas aeruginosa* bacteria with an exogenous DNA encoding the ClpP, ClpP2, or ClpX polypeptide to overexpress the ClpP, ClpP2, or ClpX polypeptide as compared to wild-type *Pseudomonas aeruginosa* bacteria and wherein the bacteria further have at least one characteristic selected from the group consisting of:
   (i) increased positive regulator activity of a MucE polypeptide as compared to wild-type *Pseudomonas aeruginosa* bacteria, wherein the increased MucE regulator activity is the result of transformation of the *Pseudomonas aeruginosa* bacteria with an exogenous DNA encoding the MucE polypeptide to overexpress the MucE polypeptide as compared to wild-type *Pseudomonas aeruginosa* bacteria,
   (ii) decreased negative regulator activity of a MucA polypeptide as compared to wild-type *Pseudomonas aeruginosa* bacteria, wherein the decreased MucA regulator activity is the result of a transposon insertion in the promoter of a mucA gene of the *Pseudomonas aeruginosa* bacteria, a mutation in the MucA polypeptide that results in the MucA polypeptide lacking a portion or all of a transmembrane domain, and/or a single base deletion at T180 of the mucA gene of the *Pseudomonas aeruginosa* bacteria, and
   (iii) lack of expression of a lipopolysaccharide do not express at least one endotoxin biosynthesis gene.

2. The biological culture of claim 1, wherein the alginate is acetylated and the degree of acetylation is 0.1 to 1.0.

3. The biological culture of claim 1, wherein the ratio of M blocks to G blocks in the alginate is between 1:10 and 10:1.

4. The biological culture of claim 1, wherein the molecular weight of the alginate is between 500 and 20,000 kD.

5. A method for producing alginate comprising: (a) culturing the biological culture of claim 1 to produce alginate; and (b) isolating the alginate.

6. The method of claim 5, wherein the *Pseudomonas aeruginosa* bacteria is transformed with a plasmid encoding a MucE polypeptide and wherein the MucE polypeptide is expressed from the plasmid.

7. A biological culture comprising isolated stable mucoid *Pseudomonas aeruginosa* bacteria that produce alginate, wherein the bacteria are genetically modified *Pseudomonas aeruginosa* bacteria having increased protease activity of a ClpP, ClpP2, or ClpX polypeptide as compared to wild-type *Pseudomonas aeruginosa* bacteria that is the result of transformation of the *Pseudomonas aeruginosa* bacteria with an exogenous DNA encoding the ClpP, ClpP2, or ClpX polypeptide to overexpress the ClpP, ClpP2, or ClpX polypeptide as compared to wild-type *Pseudomonas aeruginosa* bacteria.

8. The biological culture of claim 1, wherein the stable mucoid *Pseudomonas aeruginosa* bacteria further comprises a C-terminal deletion in a MucA polypeptide resulting in the MucA polypeptide having 20 to 160 amino acids.

9. The biological culture of claim 1, wherein the stable mucoid *Pseudomonas aeruginosa* bacteria are stable for 14 to 90 days.

* * * * *

SEQUENCE LISTING

```
<160> NUMBER OF SEQ ID NOS: 12

<210> SEQ ID NO 1
<211> LENGTH: 89
<212> TYPE: PRT
<213> ORGANISM: Pseudomonas aeruginosa

<400> SEQUENCE: 1

Met Gly Phe Arg Pro Val Ser Gln Arg Leu Arg Asp Ile Asn Leu Gln
1               5                   10                  15

Ala Leu Gly Lys Phe Ser Cys Leu Ala Leu Val Leu Gly Leu Glu Ser
            20                  25                  30

Val Ser His Pro Ala Gly Pro Val Gln Ala Pro Ser Phe Ser Gln Gly
        35                  40                  45

Thr Ala Ser Pro Ser Phe Ala Thr Pro Leu Gly Leu Asp Gly Pro Ala
    50                  55                  60
```

Arg Ala Arg Ala Glu Met Trp Asn Val Gly Leu Ser Gly Ala Val Ser
65                  70                  75                  80

Val Arg Asp Glu Leu Arg Trp Val Phe
                85

<210> SEQ ID NO 2
<211> LENGTH: 89
<212> TYPE: PRT
<213> ORGANISM: Pseudomonas aeruginosa

<400> SEQUENCE: 2

Met Gly Phe Arg Pro Val Ser Gln Arg Leu Arg Asp Ile Asn Leu Gln
1               5                   10                  15

Ala Leu Gly Lys Phe Ser Cys Leu Ala Leu Val Leu Gly Leu Glu Ser
                20                  25                  30

Val Ser His Pro Ala Gly Pro Val Gln Ala Pro Ser Phe Ser Gln Gly
            35                  40                  45

Thr Ala Ser Pro Ser Phe Ala Thr Pro Leu Gly Leu Asp Gly Pro Ala
        50                  55                  60

Arg Ala Arg Ala Glu Met Trp Asn Val Gly Leu Ser Gly Ala Val Ser
65                  70                  75                  80

Val Arg Asp Glu Leu Arg Trp Val Phe
                85

<210> SEQ ID NO 3
<211> LENGTH: 89
<212> TYPE: PRT
<213> ORGANISM: Pseudomonas aeruginosa

<400> SEQUENCE: 3

Met Gly Phe Arg Pro Val Ser Gln Arg Leu Arg Asp Ile Asn Leu Gln
1               5                   10                  15

Ala Leu Gly Lys Phe Ser Cys Leu Ala Leu Val Leu Gly Leu Glu Ser
                20                  25                  30

Val Ser His Pro Ala Gly Pro Val Gln Ala Pro Ser Phe Ser Gln Gly
            35                  40                  45

Thr Ala Ser Pro Ser Phe Ala Thr Pro Leu Gly Leu Asp Gly Pro Ala
        50                  55                  60

Arg Ala Arg Ala Glu Met Trp Asn Val Gly Leu Ser Gly Ala Val Ser
65                  70                  75                  80

Val Arg Asp Glu Leu Arg Trp Val Phe
                85

<210> SEQ ID NO 4
<211> LENGTH: 89
<212> TYPE: PRT
<213> ORGANISM: Pseudomonas aeruginosa

<400> SEQUENCE: 4

Met Gly Phe Arg Pro Val Ser Gln Arg Leu Arg Asp Ile Asn Leu Gln
1               5                   10                  15

Ala Leu Gly Lys Phe Ser Cys Leu Ala Leu Val Leu Gly Leu Glu Ser
                20                  25                  30

Val Ser His Pro Ala Gly Pro Val Gln Ala Pro Ser Phe Ser Gln Gly
            35                  40                  45

Thr Ala Ser Pro Ser Phe Ala Thr Pro Leu Gly Leu Asp Gly Pro Ala
        50                  55                  60

```
Arg Ala Arg Ala Glu Met Trp Asn Val Gly Leu Ser Gly Ala Val Ser
 65                  70                  75                  80

Val Arg Asp Glu Leu Arg Trp Val Phe
                 85

<210> SEQ ID NO 5
<211> LENGTH: 79
<212> TYPE: PRT
<213> ORGANISM: Pseudomonas fluorescens

<400> SEQUENCE: 5

Met Asn Ser Ala Leu Leu Leu Asn Ala Ile Ala Ile Ala Val Leu
 1               5                  10                  15

Ala Ala Phe His Phe Gln Pro Ala Asp Asp Ala Ala Pro Gly Gly Thr
                 20                  25                  30

Ser Phe Ala His Tyr Gln Gln Arg Leu Ala Pro Gln Leu Ala Val Met
                 35                  40                  45

Asn Thr Gln Ile Glu Pro Gly Ser Val Thr Arg Val Thr Gln Gly Lys
             50                  55                  60

Ala Ser Gln Gln Pro Ala Ala Pro Thr Glu Arg Trp Val Phe
 65                  70                  75

<210> SEQ ID NO 6
<211> LENGTH: 75
<212> TYPE: PRT
<213> ORGANISM: Pseudomonas fluorescens

<400> SEQUENCE: 6

Met Asn Ser Ala Leu Val Phe Ala Asn Ala Ile Ala Leu Ala Val Leu
 1               5                  10                  15

Met Gly Phe His Leu Val Pro Glu Asp Asn Glu Lys Val Ala Gly Arg
                 20                  25                  30

Met Pro His Tyr Leu Gln Val Gln Lys Ala Pro Gln Trp Ala Val Leu
                 35                  40                  45

Ser Asp Gln Ser Phe Ala Pro Gln Ala Val Ser Gln Ser Glu Gln Ala
             50                  55                  60

Leu Pro Ala His Ser Thr Glu Arg Leu Val Phe
 65                  70                  75

<210> SEQ ID NO 7
<211> LENGTH: 79
<212> TYPE: PRT
<213> ORGANISM: Pseudomonas syringae

<400> SEQUENCE: 7

Met Asn Lys Thr Leu Ser Val Leu Asn Ala Ala Ala Leu Val Ala Leu
 1               5                  10                  15

Val Ala Phe His Phe His Asp Ser Gly Ala Ser Asp Thr Gln Val Asn
                 20                  25                  30

Ala Pro Ala Pro Val His His Gln Ile Ser His Ala Pro Gln Leu Ala
                 35                  40                  45

Ile Met Thr Asp Arg Ile Ala Ser Ala Ala Val Leu Ala Asn Asp Asp
             50                  55                  60

Asp Asp Ser Leu Gln Met Pro Arg Ala Glu Gln Arg Trp Ile Phe
 65                  70                  75
```

<210> SEQ ID NO 8
<211> LENGTH: 79
<212> TYPE: PRT
<213> ORGANISM: Pseudomonas syringae

<400> SEQUENCE: 8

Met Asn Lys Thr Leu Ser Ala Leu Asn Ala Ala Leu Val Ala Leu
1               5                   10                  15

Val Ala Phe His Phe Gln Asp Ser Gly Ala Lys Asp Thr Gln Val Thr
            20                  25                  30

Ala Pro Ala Pro Val His His Gln Ile Ser His Ala Pro Gln Leu Ala
        35                  40                  45

Ile Met Thr Asp Arg Val Ala Ser Ala Ala Val Leu Ala Thr Asp Asp
    50                  55                  60

Asp Ala Ser Val Gln Met Pro Arg Ala Glu Gln Arg Trp Val Phe
65                  70                  75

<210> SEQ ID NO 9
<211> LENGTH: 79
<212> TYPE: PRT
<213> ORGANISM: Pseudomonas syringae

<400> SEQUENCE: 9

Met Asn Lys Thr Leu Ser Ala Leu Asn Ala Ala Leu Val Ala Leu
1               5                   10                  15

Val Ala Phe His Phe Gln Asp Ser Gly Ile Lys Asp Ala Gln Ala Ile
            20                  25                  30

Thr Pro Ala Pro Val His His Gln Ile Ser Gln Ala Pro Lys Leu Ala
        35                  40                  45

Ile Met Thr Asp Arg Val Ala Ser Ala Ala Met Leu Ala Asn Asp Asp
    50                  55                  60

Asp Glu Ser Leu Gln Phe Pro Arg Ala Glu Gln Arg Trp Val Phe
65                  70                  75

<210> SEQ ID NO 10
<211> LENGTH: 89
<212> TYPE: PRT
<213> ORGANISM: Artificial
<220> FEATURE:
<223> OTHER INFORMATION: Pseudomonas mucE consensus sequence
<220> FEATURE:
<221> NAME/KEY: misc_feature
<222> LOCATION: (1)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (19)..(37)
<223> OTHER INFORMATION: Xaa can be any naturally occurring amino acid
<220> FEATURE:
<221> NAME/KEY: misc_feature
<222> LOCATION: (40)..(42)
<223> OTHER INFORMATION: Xaa can be any naturally occurring amino acid
<220> FEATURE:
<221> NAME/KEY: misc_feature
<222> LOCATION: (44)..(46)
<223> OTHER INFORMATION: Xaa can be any naturally occurring amino acid

```
<220> FEATURE:
<221> NAME/KEY: misc_feature
<222> LOCATION: (48)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(67)
<223> OTHER INFORMATION: Xaa can be any naturally occurring amino acid
<220> FEATURE:
<221> NAME/KEY: misc_feature
<222> LOCATION: (69)..(71)
<223> OTHER INFORMATION: Xaa can be any naturally occurring amino acid
<220> FEATURE:
<221> NAME/KEY: misc_feature
<222> LOCATION: (73)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid

<400> SEQUENCE: 10

Xaa Xaa Xaa Xaa Xaa Xaa Xaa Xaa Xaa Leu Xaa Xaa Xaa Asn Xaa Xaa
1               5                   10                  15

Ala Leu Xaa Xaa Xaa Xaa Xaa Xaa Xaa Xaa Xaa Xaa Xaa Xaa
            20                  25                  30

Xaa Xaa Xaa Xaa Xaa Gly Pro Xaa Xaa Xaa Pro Xaa Xaa Xaa Gln Xaa
        35                  40                  45

Xaa Xaa Xaa Pro Xaa Xaa Ala Xaa Xaa Xaa Xaa Xaa Xaa Xaa Xaa
    50                  55                  60

Xaa Xaa Xaa Ala Xaa Xaa Xaa Asn Xaa Xaa Xaa Xaa Xaa Xaa Xaa Xaa
65                  70                  75                  80

Xaa Arg Xaa Glu Xaa Arg Trp Val Phe
                85

<210> SEQ ID NO 11
<211> LENGTH: 29
<212> TYPE: DNA
<213> ORGANISM: Artificial Sequence
<220> FEATURE:
<223> OTHER INFORMATION: Inverted repeat region of mariner transposon
      vector

<400> SEQUENCE: 11
taacaggttg gctgataagt ccccggtct                                    29

<210> SEQ ID NO 12
<211> LENGTH: 29
<212> TYPE: DNA
<213> ORGANISM: Artificial Sequence
<220> FEATURE:
<223> OTHER INFORMATION: Inverted repeat region of mariner transposon
      vector

<400> SEQUENCE: 12
agaccgggga cttatcagcc aacctgtta                                    29
```